(12) United States Patent
Kim et al.

(10) Patent No.: US 11,851,465 B2
(45) Date of Patent: Dec. 26, 2023

(54) METHOD FOR REGULATING SECRETION ABILITY OF HOMEOPROTEINS AND THEIR VARIANTS HAVING ALTERED SECRETION ABILITY

(71) Applicant: KOREA ADVANCED INSTITUTE OF SCIENCE AND TECHNOLOGY, Daejeon (KR)

(72) Inventors: Jin Woo Kim, Daejeon (KR); Eun Jung Lee, Daejeon (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 115 days.

(21) Appl. No.: 17/110,924

(22) Filed: Dec. 3, 2020

(65) Prior Publication Data

US 2021/0163554 A1 Jun. 3, 2021

(30) Foreign Application Priority Data

Dec. 3, 2019 (KR) ......................... 10-2019-0159210

(51) Int. Cl.
*C07K 14/47* (2006.01)
(52) U.S. Cl.
CPC ................. *C07K 14/4702* (2013.01)
(58) Field of Classification Search
None
See application file for complete search history.

(56) References Cited

FOREIGN PATENT DOCUMENTS

KR 10-1106262 B1 1/2012

OTHER PUBLICATIONS

Sahni et al. (Cell. Apr. 23, 2015; 161(3): 647-660) (Year: 2015).*
GenBank AKI71259.1 (OTX2, Jun. 1, 2015) (Year: 2015).*
Eun Jung Lee et al., "Global Analysis of Intercellular Homeodomain Protein Transfer", Cell Reports 28, Jul. 16, 2019, pp. 712-722.
Alexis Maizel et al., "Engrailed homeoprotein secretion is a regulated process", Development 129, Apr. 30, 2002, pp. 3545-3553.

* cited by examiner

*Primary Examiner* — Sergio Coffa
(74) *Attorney, Agent, or Firm* — Paratus Law Group, PLLC

(57) ABSTRACT

Disclosed is a method for regulating the extracellular secretion ability of a homeoprotein and a homeoprotein variant having regulated extracellular secretion ability using the same, and more particularly, a method for increasing or decreasing the extracellular secretion ability through the increase or decrease in hydrophobicity of an amino acid sequence among homeodomain external amino acid sequences, or a homeoprotein whose extracellular secretion ability is increased or decreased through the increase or decrease in hydrophobicity of the homeodomain external amino acid sequence.

8 Claims, 11 Drawing Sheets

Specification includes a Sequence Listing.

SEQUENCE LISTING

```
<160> NUMBER OF SEQ ID NOS: 13

<210> SEQ ID NO 1
<211> LENGTH: 255
<212> TYPE: PRT
<213> ORGANISM: Homo sapiens
<220> FEATURE:
<221> NAME/KEY: HOXD4
<222> LOCATION: (1)..(255)

<400> SEQUENCE: 1

Met Val Met Ser Ser Tyr Met Val Asn Ser Lys Tyr Val Asp Pro Lys
1               5                   10                  15

Phe Pro Pro Cys Glu Glu Tyr Leu Gln Gly Gly Tyr Leu Gly Glu Gln
            20                  25                  30
```

```
Gly Ala Asp Tyr Tyr Gly Gly Ala Gln Gly Ala Asp Phe Gln Pro
            35                  40                  45
Pro Gly Leu Tyr Pro Arg Pro Asp Phe Gly Glu Gln Pro Phe Gly Gly
 50                  55                  60
Ser Gly Pro Gly Pro Gly Ser Ala Leu Pro Ala Arg Gly His Gly Gln
 65                  70                  75                  80
Glu Pro Gly Gly Pro Gly Gly His Tyr Ala Ala Pro Gly Glu Pro Cys
                    85                  90                  95
Pro Ala Pro Ala Pro Pro Ala Pro Leu Pro Gly Ala Arg Ala
                100                 105                 110
Tyr Ser Gln Ser Asp Pro Lys Gln Pro Pro Ser Gly Thr Ala Leu Lys
                115                 120                 125
Gln Pro Ala Val Val Tyr Pro Trp Met Lys Lys Val His Val Asn Ser
 130                 135                 140
Val Asn Pro Asn Tyr Thr Gly Gly Glu Pro Lys Arg Ser Arg Thr Ala
 145                 150                 155                 160
Tyr Thr Arg Gln Gln Val Leu Glu Leu Glu Lys Glu Phe His Phe Asn
                165                 170                 175
Arg Tyr Leu Thr Arg Arg Arg Ile Glu Ile Ala His Thr Leu Cys
                180                 185                 190
Leu Ser Glu Arg Gln Ile Lys Ile Trp Phe Gln Asn Arg Arg Met Lys
                195                 200                 205
Trp Lys Lys Asp His Lys Leu Pro Asn Thr Lys Gly Arg Ser Ser Ser
 210                 215                 220
Ser Ser Ser Ser Ser Cys Ser Ser Ser Val Ala Pro Ser Gln His
 225                 230                 235                 240
Leu Gln Pro Met Ala Lys Asp His His Thr Asp Leu Thr Thr Leu
                245                 250                 255

<210> SEQ ID NO 2
<211> LENGTH: 355
<212> TYPE: PRT
<213> ORGANISM: Homo sapiens
<220> FEATURE:
<221> NAME/KEY: SHOX2
<222> LOCATION: (1)..(355)

<400> SEQUENCE: 2

Met Glu Glu Leu Thr Ala Phe Val Ser Lys Ser Phe Asp Gln Lys Val
 1                   5                  10                  15
Lys Glu Lys Lys Glu Ala Ile Thr Tyr Arg Glu Val Leu Glu Ser Gly
                20                  25                  30
Pro Leu Arg Gly Ala Lys Glu Pro Thr Gly Cys Thr Glu Ala Gly Arg
                35                  40                  45
Asp Asp Arg Ser Ser Pro Ala Val Arg Ala Ala Gly Gly Gly Gly
  50                  55                  60
Gly Gly Gly Gly Gly Gly Gly Gly Gly Gly Val Gly Gly
 65                  70                  75                  80
Gly Gly Ala Gly Gly Ala Gly Gly Arg Ser Pro Val Arg Glu
                85                  90                  95
Leu Asp Met Gly Ala Ala Glu Arg Ser Arg Glu Pro Gly Ser Pro Arg
                100                 105                 110
Leu Thr Glu Gly Arg Arg Lys Pro Thr Lys Ala Glu Val Gln Ala Thr
                115                 120                 125
Leu Leu Leu Pro Gly Glu Ala Phe Arg Phe Leu Val Ser Pro Glu Leu
 130                 135                 140
```

```
Lys Asp Arg Lys Glu Asp Ala Lys Gly Met Glu Asp Glu Gly Gln Thr
145                 150                 155                 160

Lys Ile Lys Gln Arg Arg Ser Arg Thr Asn Phe Thr Leu Glu Gln Leu
                165                 170                 175

Asn Glu Leu Glu Arg Leu Phe Asp Glu Thr His Tyr Pro Asp Ala Phe
            180                 185                 190

Met Arg Glu Glu Leu Ser Gln Arg Leu Gly Leu Ser Glu Ala Arg Val
        195                 200                 205

Gln Val Trp Phe Gln Asn Arg Arg Ala Lys Cys Arg Lys Gln Glu Asn
    210                 215                 220

Gln Leu His Lys Gly Val Leu Ile Gly Ala Ala Ser Gln Phe Glu Ala
225                 230                 235                 240

Cys Arg Val Ala Pro Tyr Val Asn Val Gly Ala Leu Arg Met Pro Phe
                245                 250                 255

Gln Gln Asp Ser His Cys Asn Val Thr Pro Leu Ser Phe Gln Val Gln
            260                 265                 270

Ala Gln Leu Gln Leu Asp Ser Ala Val Ala His Ala His His His Leu
        275                 280                 285

His Pro His Leu Ala Ala His Ala Pro Tyr Met Met Phe Pro Ala Pro
    290                 295                 300

Pro Phe Gly Leu Pro Leu Ala Thr Leu Ala Ala Asp Ser Ala Ser Ala
305                 310                 315                 320

Ala Ser Val Val Ala Ala Ala Ala Ala Lys Thr Thr Ser Lys Asn
                325                 330                 335

Ser Ser Ile Ala Asp Leu Arg Leu Lys Ala Lys Lys His Ala Ala Ala
                340                 345                 350

Leu Gly Leu
        355

<210> SEQ ID NO 3
<211> LENGTH: 333
<212> TYPE: PRT
<213> ORGANISM: Homo sapiens
<220> FEATURE:
<221> NAME/KEY: EN2
<222> LOCATION: (1)..(333)

<400> SEQUENCE: 3

Met Glu Glu Asn Asp Pro Lys Pro Gly Glu Ala Ala Ala Ala Val Glu
1               5                   10                  15

Gly Gln Arg Gln Pro Glu Ser Ser Pro Gly Gly Gly Ser Gly Gly Gly
                20                  25                  30

Gly Gly Ser Ser Pro Gly Glu Ala Asp Thr Gly Arg Arg Arg Ala Leu
            35                  40                  45

Met Leu Pro Ala Val Leu Gln Ala Pro Gly Asn His Gln His Pro His
        50                  55                  60

Arg Ile Thr Asn Phe Phe Ile Asp Asn Ile Leu Arg Pro Glu Phe Gly
65                  70                  75                  80

Arg Arg Lys Asp Ala Gly Thr Cys Cys Ala Gly Ala Gly Gly Gly Arg
                85                  90                  95

Gly Gly Gly Ala Gly Gly Glu Gly Ala Ser Gly Ala Glu Gly Gly
                100                 105                 110

Gly Gly Ala Gly Gly Ser Glu Gln Leu Leu Gly Ser Gly Ser Arg Glu
            115                 120                 125

Pro Arg Gln Asn Pro Pro Cys Ala Pro Gly Ala Gly Gly Pro Leu Pro
```

```
                    130                 135                 140
Ala Ala Gly Ser Asp Ser Pro Gly Asp Gly Glu Gly Ser Lys Thr
145                 150                 155                 160

Leu Ser Leu His Gly Gly Ala Lys Lys Gly Asp Pro Gly Gly Pro
                    165                 170                 175

Leu Asp Gly Ser Leu Lys Ala Arg Gly Leu Gly Gly Gly Asp Leu Ser
                    180                 185                 190

Val Ser Ser Asp Ser Asp Ser Ser Gln Ala Gly Ala Asn Leu Gly Ala
                    195                 200                 205

Gln Pro Met Leu Trp Pro Ala Trp Val Tyr Cys Thr Arg Tyr Ser Asp
                210                 215                 220

Arg Pro Ser Ser Gly Pro Arg Ser Arg Lys Pro Lys Lys Asn Pro
225                 230                 235                 240

Asn Lys Glu Asp Lys Arg Pro Arg Thr Ala Phe Thr Ala Glu Gln Leu
                    245                 250                 255

Gln Arg Leu Lys Ala Glu Phe Gln Thr Asn Arg Tyr Leu Thr Glu Gln
                    260                 265                 270

Arg Arg Gln Ser Leu Ala Gln Glu Leu Ser Leu Asn Glu Ser Gln Ile
                275                 280                 285

Lys Ile Trp Phe Gln Asn Lys Arg Ala Lys Ile Lys Lys Ala Thr Gly
                290                 295                 300

Asn Lys Asn Thr Leu Ala Val His Leu Met Ala Gln Gly Leu Tyr Asn
305                 310                 315                 320

His Ser Thr Thr Ala Lys Glu Gly Lys Ser Asp Ser Glu
                    325                 330

<210> SEQ ID NO 4
<211> LENGTH: 297
<212> TYPE: PRT
<213> ORGANISM: Homo sapiens
<220> FEATURE:
<221> NAME/KEY: OTX2
<222> LOCATION: (1)..(297)

<400> SEQUENCE: 4

Met Met Ser Tyr Leu Lys Gln Pro Pro Tyr Ala Val Asn Gly Leu Ser
1               5                   10                  15

Leu Thr Thr Ser Gly Met Asp Leu Leu His Pro Ser Val Gly Tyr Pro
                20                  25                  30

Gly Pro Trp Ala Ser Cys Pro Ala Ala Thr Pro Arg Lys Gln Arg Arg
                35                  40                  45

Glu Arg Thr Thr Phe Thr Arg Ala Gln Leu Asp Val Leu Glu Ala Leu
                50                  55                  60

Phe Ala Lys Thr Arg Tyr Pro Asp Ile Phe Met Arg Glu Glu Val Ala
65                  70                  75                  80

Leu Lys Ile Asn Leu Pro Glu Ser Arg Val Gln Val Trp Phe Lys Asn
                    85                  90                  95

Arg Arg Ala Lys Cys Arg Gln Gln Gln Gln Gln Gln Asn Gly Gly
                100                 105                 110

Gln Asn Lys Val Arg Pro Ala Lys Lys Lys Thr Ser Pro Ala Arg Glu
                115                 120                 125

Val Ser Ser Glu Ser Gly Thr Ser Gly Gln Phe Thr Pro Pro Ser Ser
            130                 135                 140

Thr Ser Val Pro Thr Ile Ala Ser Ser Ala Pro Val Ser Ile Trp
145                 150                 155                 160
```

```
Ser Pro Ala Ser Ile Ser Pro Leu Ser Asp Pro Leu Ser Thr Ser Ser
                165                 170                 175

Ser Cys Met Gln Arg Ser Tyr Pro Met Thr Tyr Thr Gln Ala Ser Gly
        180                 185                 190

Tyr Ser Gln Gly Tyr Ala Gly Ser Thr Ser Tyr Phe Gly Gly Met Asp
        195                 200                 205

Cys Gly Ser Tyr Leu Thr Pro Met His His Gln Leu Pro Gly Pro Gly
    210                 215                 220

Ala Thr Leu Ser Pro Met Gly Thr Asn Ala Val Thr Ser His Leu Asn
225                 230                 235                 240

Gln Ser Pro Ala Ser Leu Ser Thr Gln Gly Tyr Gly Ala Ser Ser Leu
                245                 250                 255

Gly Phe Asn Ser Thr Thr Asp Cys Leu Asp Tyr Lys Asp Gln Thr Ala
            260                 265                 270

Ser Trp Lys Leu Asn Phe Asn Ala Asp Cys Leu Asp Tyr Lys Asp Gln
        275                 280                 285

Thr Ser Ser Trp Lys Phe Gln Val Leu
            290                 295

<210> SEQ ID NO 5
<211> LENGTH: 422
<212> TYPE: PRT
<213> ORGANISM: Homo sapiens
<220> FEATURE:
<221> NAME/KEY: PAX6
<222> LOCATION: (1)..(422)

<400> SEQUENCE: 5

Met Gln Asn Ser His Ser Gly Val Asn Gln Leu Gly Gly Val Phe Val
1               5                   10                  15

Asn Gly Arg Pro Leu Pro Asp Ser Thr Arg Gln Lys Ile Val Glu Leu
            20                  25                  30

Ala His Ser Gly Ala Arg Pro Cys Asp Ile Ser Arg Ile Leu Gln Val
        35                  40                  45

Ser Asn Gly Cys Val Ser Lys Ile Leu Gly Arg Tyr Tyr Glu Thr Gly
    50                  55                  60

Ser Ile Arg Pro Arg Ala Ile Gly Gly Ser Lys Pro Arg Val Ala Thr
65                  70                  75                  80

Pro Glu Val Val Ser Lys Ile Ala Gln Tyr Lys Arg Glu Cys Pro Ser
                85                  90                  95

Ile Phe Ala Trp Glu Ile Arg Asp Arg Leu Leu Ser Glu Gly Val Cys
            100                 105                 110

Thr Asn Asp Asn Ile Pro Ser Val Ser Ser Ile Asn Arg Val Leu Arg
        115                 120                 125

Asn Leu Ala Ser Glu Lys Gln Gln Met Gly Ala Asp Gly Met Tyr Asp
    130                 135                 140

Lys Leu Arg Met Leu Asn Gly Gln Thr Gly Ser Trp Gly Thr Arg Pro
145                 150                 155                 160

Gly Trp Tyr Pro Gly Thr Ser Val Pro Gly Gln Pro Thr Gln Asp Gly
                165                 170                 175

Cys Gln Gln Gln Glu Gly Gly Gly Glu Asn Thr Asn Ser Ile Ser Ser
            180                 185                 190

Asn Gly Glu Asp Ser Asp Glu Ala Gln Met Arg Leu Gln Leu Lys Arg
        195                 200                 205

Lys Leu Gln Arg Asn Arg Thr Ser Phe Thr Gln Glu Gln Ile Glu Ala
    210                 215                 220
```

```
Leu Glu Lys Glu Phe Glu Arg Thr His Tyr Pro Asp Val Phe Ala Arg
225                 230                 235                 240

Glu Arg Leu Ala Ala Lys Ile Asp Leu Pro Glu Ala Arg Ile Gln Val
            245                 250                 255

Trp Phe Ser Asn Arg Arg Ala Lys Trp Arg Arg Glu Glu Lys Leu Arg
        260                 265                 270

Asn Gln Arg Arg Gln Ala Ser Asn Thr Pro Ser His Ile Pro Ile Ser
    275                 280                 285

Ser Ser Phe Ser Thr Ser Val Tyr Gln Pro Ile Pro Gln Pro Thr Thr
290                 295                 300

Pro Val Ser Ser Phe Thr Ser Gly Ser Met Leu Gly Arg Thr Asp Thr
305                 310                 315                 320

Ala Leu Thr Asn Thr Tyr Ser Ala Leu Pro Pro Met Pro Ser Phe Thr
                325                 330                 335

Met Ala Asn Asn Leu Pro Met Gln Pro Pro Val Pro Ser Gln Thr Ser
            340                 345                 350

Ser Tyr Ser Cys Met Leu Pro Thr Ser Pro Ser Val Asn Gly Arg Ser
        355                 360                 365

Tyr Asp Thr Tyr Thr Pro Pro His Met Gln Thr His Met Asn Ser Gln
    370                 375                 380

Pro Met Gly Thr Ser Gly Thr Thr Ser Thr Gly Leu Ile Ser Pro Gly
385                 390                 395                 400

Val Ser Val Pro Val Gln Val Pro Gly Ser Glu Pro Asp Met Ser Gln
                405                 410                 415

Tyr Trp Pro Arg Leu Gln
            420

<210> SEQ ID NO 6
<211> LENGTH: 336
<212> TYPE: PRT
<213> ORGANISM: Homo sapiens
<220> FEATURE:
<221> NAME/KEY: VAX1
<222> LOCATION: (1)..(336)

<400> SEQUENCE: 6

Met Phe Gly Lys Thr Asp Lys Met Asp Val Arg Cys His Ser Asp Thr
1               5                   10                  15

Glu Ala Ala Arg Val Ser Lys Asn Ala His Lys Glu Ser Arg Glu Ile
            20                  25                  30

Lys Gly Ala Glu Gly Ser Leu Pro Ala Ala Phe Leu Lys Glu Pro Gln
        35                  40                  45

Gly Ala Phe Ser Ala Ser Gly Ala Ser Glu Asp Cys Asn Lys Ser Lys
    50                  55                  60

Ser Asn Ser Ser Ala Asp Pro Asp Tyr Cys Arg Arg Ile Leu Val Arg
65                  70                  75                  80

Asp Ala Lys Gly Ser Ile Arg Glu Ile Ile Leu Pro Lys Gly Leu Asp
                85                  90                  95

Leu Asp Arg Pro Lys Arg Thr Arg Thr Ser Phe Thr Ala Glu Gln Leu
            100                 105                 110

Tyr Arg Leu Glu Met Glu Phe Gln Arg Cys Gln Tyr Val Val Gly Arg
        115                 120                 125

Glu Arg Thr Glu Leu Ala Arg Gln Leu Asn Leu Ser Glu Thr Gln Val
    130                 135                 140

Lys Val Trp Phe Gln Asn Arg Arg Thr Lys Gln Lys Lys Asp Gln Gly
```

```
                145                 150                 155                 160
Lys Asp Ser Glu Leu Arg Ser Val Val Ser Glu Thr Ala Ala Thr Cys
                    165                 170                 175

Ser Val Leu Arg Leu Leu Glu Gln Gly Arg Leu Leu Ser Pro Pro Gly
                    180                 185                 190

Leu Pro Ala Leu Leu Pro Pro Cys Ala Thr Gly Ala Leu Gly Ser Ala
                    195                 200                 205

Leu Arg Gly Pro Ser Leu Pro Ala Leu Gly Ala Gly Ala Ala Ala Gly
            210                 215                 220

Ser Ala Ala Ala Ala Ala Ala Ala Thr Ala Pro Gly Pro Ala Gly
225                 230                 235                 240

Ala Ala Ser Gln His Pro Pro Ala Val Gly Ala Pro Gly Pro Gly
                245                 250                 255

Pro Ala Gly Pro Gly Gly Leu His Ala Gly Ala Pro Thr Ala Ser His
                    260                 265                 270

Gly Leu Phe Ser Leu Pro Val Pro Ser Leu Leu Gly Ser Val Ala Ser
                    275                 280                 285

Arg Leu Ser Ser Ala Pro Leu Thr Met Ala Gly Ser Leu Ala Gly Asn
                290                 295                 300

Leu Gln Glu Leu Ser Ala Arg Tyr Leu Ser Ser Ser Ala Phe Glu Pro
305                 310                 315                 320

Tyr Ser Arg Thr Asn Asn Lys Glu Gly Ala Glu Lys Lys Ala Leu Asp
                325                 330                 335

<210> SEQ ID NO 7
<211> LENGTH: 255
<212> TYPE: PRT
<213> ORGANISM: Artificial Sequence
<220> FEATURE:
<223> OTHER INFORMATION: HOXD4 (S233L)

<400> SEQUENCE: 7

Met Val Met Ser Ser Tyr Met Val Asn Ser Lys Tyr Val Asp Pro Lys
1               5                   10                  15

Phe Pro Pro Cys Glu Glu Tyr Leu Gln Gly Gly Tyr Leu Gly Glu Gln
                20                  25                  30

Gly Ala Asp Tyr Tyr Gly Gly Ala Gln Gly Ala Asp Phe Gln Pro
            35                  40                  45

Pro Gly Leu Tyr Pro Arg Pro Asp Phe Gly Glu Gln Pro Phe Gly Gly
            50                  55                  60

Ser Gly Pro Gly Pro Gly Ser Ala Leu Pro Ala Arg Gly His Gly Gln
65              70                  75                  80

Glu Pro Gly Gly Pro Gly Gly His Tyr Ala Ala Pro Gly Glu Pro Cys
                85                  90                  95

Pro Ala Pro Pro Ala Pro Pro Ala Pro Leu Pro Gly Ala Arg Ala
                100                 105                 110

Tyr Ser Gln Ser Asp Pro Lys Gln Pro Pro Ser Gly Thr Ala Leu Lys
            115                 120                 125

Gln Pro Ala Val Val Tyr Pro Trp Met Lys Lys Val His Val Asn Ser
        130                 135                 140

Val Asn Pro Asn Tyr Thr Gly Gly Glu Pro Lys Arg Ser Arg Thr Ala
145                 150                 155                 160

Tyr Thr Arg Gln Gln Val Leu Glu Leu Glu Lys Glu Phe His Phe Asn
                165                 170                 175

Arg Tyr Leu Thr Arg Arg Arg Arg Ile Glu Ile Ala His Thr Leu Cys
```

```
                    180                 185                 190
Leu Ser Glu Arg Gln Ile Lys Ile Trp Phe Gln Asn Arg Arg Met Lys
                195                 200                 205

Trp Lys Lys Asp His Lys Leu Pro Asn Thr Lys Gly Arg Ser Ser Ser
            210                 215                 220

Ser Ser Ser Ser Ser Ser Cys Ser Leu Ser Val Ala Pro Ser Gln His
225                 230                 235                 240

Leu Gln Pro Met Ala Lys Asp His His Thr Asp Leu Thr Thr Leu
                245                 250                 255

<210> SEQ ID NO 8
<211> LENGTH: 355
<212> TYPE: PRT
<213> ORGANISM: Artificial Sequence
<220> FEATURE:
<223> OTHER INFORMATION: SHOX2 (P305L)

<400> SEQUENCE: 8

Met Glu Glu Leu Thr Ala Phe Val Ser Lys Ser Phe Asp Gln Lys Val
1               5                   10                  15

Lys Glu Lys Lys Glu Ala Ile Thr Tyr Arg Glu Val Leu Glu Ser Gly
            20                  25                  30

Pro Leu Arg Gly Ala Lys Glu Pro Thr Gly Cys Thr Glu Ala Gly Arg
        35                  40                  45

Asp Asp Arg Ser Ser Pro Ala Val Arg Ala Ala Gly Gly Gly Gly Gly
    50                  55                  60

Gly Gly Gly Gly Gly Gly Gly Gly Gly Gly Val Gly Gly
65                  70                  75                  80

Gly Gly Ala Gly Gly Ala Gly Gly Arg Ser Pro Val Arg Glu
                85                  90                  95

Leu Asp Met Gly Ala Ala Glu Arg Ser Arg Glu Pro Gly Ser Pro Arg
                100                 105                 110

Leu Thr Glu Gly Arg Arg Lys Pro Thr Lys Ala Glu Val Gln Ala Thr
            115                 120                 125

Leu Leu Leu Pro Gly Glu Ala Phe Arg Phe Leu Val Ser Pro Glu Leu
        130                 135                 140

Lys Asp Arg Lys Glu Asp Ala Lys Gly Met Glu Asp Glu Gly Gln Thr
145                 150                 155                 160

Lys Ile Lys Gln Arg Arg Ser Arg Thr Asn Phe Thr Leu Glu Gln Leu
                165                 170                 175

Asn Glu Leu Glu Arg Leu Phe Asp Glu Thr His Tyr Pro Asp Ala Phe
            180                 185                 190

Met Arg Glu Glu Leu Ser Gln Arg Leu Gly Leu Ser Glu Ala Arg Val
        195                 200                 205

Gln Val Trp Phe Gln Asn Arg Arg Ala Lys Cys Arg Lys Gln Glu Asn
    210                 215                 220

Gln Leu His Lys Gly Val Leu Ile Gly Ala Ala Ser Gln Phe Glu Ala
225                 230                 235                 240

Cys Arg Val Ala Pro Tyr Val Asn Val Gly Ala Leu Arg Met Pro Phe
                245                 250                 255

Gln Gln Asp Ser His Cys Asn Val Thr Pro Leu Ser Phe Gln Val Gln
            260                 265                 270

Ala Gln Leu Gln Leu Asp Ser Ala Val Ala His Ala His His Leu
        275                 280                 285

His Pro His Leu Ala Ala His Ala Pro Tyr Met Met Phe Pro Ala Pro
```

```
                 290                 295                 300

Leu Phe Gly Leu Pro Leu Ala Thr Leu Ala Ala Asp Ser Ala Ser Ala
305                 310                 315                 320

Ala Ser Val Val Ala Ala Ala Ala Lys Thr Thr Ser Lys Asn
                325                 330                 335

Ser Ser Ile Ala Asp Leu Arg Leu Lys Ala Lys His Ala Ala Ala
                340                 345                 350

Leu Gly Leu
        355

<210> SEQ ID NO 9
<211> LENGTH: 333
<212> TYPE: PRT
<213> ORGANISM: Artificial Sequence
<220> FEATURE:
<223> OTHER INFORMATION: EN2 (L143E) EN2 (L191E)

<400> SEQUENCE: 9

Met Glu Glu Asn Asp Pro Lys Pro Gly Glu Ala Ala Ala Val Glu
1               5                  10                  15

Gly Gln Arg Gln Pro Glu Ser Ser Pro Gly Gly Gly Ser Gly Gly Gly
                20                  25                  30

Gly Gly Ser Ser Pro Gly Glu Ala Asp Thr Gly Arg Arg Arg Ala Leu
            35                  40                  45

Met Leu Pro Ala Val Leu Gln Ala Pro Gly Asn His Gln His Pro His
    50                  55                  60

Arg Ile Thr Asn Phe Phe Ile Asp Asn Ile Leu Arg Pro Glu Phe Gly
65                  70                  75                  80

Arg Arg Lys Asp Ala Gly Thr Cys Cys Ala Gly Ala Gly Gly Gly Arg
                85                  90                  95

Gly Gly Gly Ala Gly Gly Glu Gly Gly Ala Ser Gly Ala Glu Gly Gly
            100                 105                 110

Gly Gly Ala Gly Gly Ser Glu Gln Leu Leu Gly Ser Gly Ser Arg Glu
        115                 120                 125

Pro Arg Gln Asn Pro Pro Cys Ala Pro Gly Ala Gly Gly Pro Glu Pro
130                 135                 140

Ala Ala Gly Ser Asp Ser Pro Gly Asp Gly Glu Gly Gly Ser Lys Thr
145                 150                 155                 160

Leu Ser Leu His Gly Gly Ala Lys Lys Gly Gly Asp Pro Gly Gly Pro
                165                 170                 175

Leu Asp Gly Ser Leu Lys Ala Arg Gly Leu Gly Gly Gly Asp Glu Ser
            180                 185                 190

Val Ser Ser Asp Ser Asp Ser Ser Gln Ala Gly Ala Asn Leu Gly Ala
        195                 200                 205

Gln Pro Met Leu Trp Pro Ala Trp Val Tyr Cys Thr Arg Tyr Ser Asp
210                 215                 220

Arg Pro Ser Ser Gly Pro Arg Ser Arg Lys Pro Lys Lys Lys Asn Pro
225                 230                 235                 240

Asn Lys Glu Asp Lys Arg Pro Arg Thr Ala Phe Thr Ala Glu Gln Leu
                245                 250                 255

Gln Arg Leu Lys Ala Glu Phe Gln Thr Asn Arg Tyr Leu Thr Glu Gln
            260                 265                 270

Arg Arg Gln Ser Leu Ala Gln Glu Leu Ser Leu Asn Glu Ser Gln Ile
        275                 280                 285

Lys Ile Trp Phe Gln Asn Lys Arg Ala Lys Ile Lys Lys Ala Thr Gly
```

```
            290                 295                 300
Asn Lys Asn Thr Leu Ala Val His Leu Met Ala Gln Gly Leu Tyr Asn
305                 310                 315                 320

His Ser Thr Thr Ala Lys Glu Gly Lys Ser Asp Ser Glu
                325                 330

<210> SEQ ID NO 10
<211> LENGTH: 297
<212> TYPE: PRT
<213> ORGANISM: Artificial Sequence
<220> FEATURE:
<223> OTHER INFORMATION: OTX2 (L220E)

<400> SEQUENCE: 10

Met Met Ser Tyr Leu Lys Gln Pro Pro Tyr Ala Val Asn Gly Leu Ser
1               5                   10                  15

Leu Thr Thr Ser Gly Met Asp Leu Leu His Pro Ser Val Gly Tyr Pro
                20                  25                  30

Gly Pro Trp Ala Ser Cys Pro Ala Ala Thr Pro Arg Lys Gln Arg Arg
            35                  40                  45

Glu Arg Thr Thr Phe Thr Arg Ala Gln Leu Asp Val Leu Glu Ala Leu
50                  55                  60

Phe Ala Lys Thr Arg Tyr Pro Asp Ile Phe Met Arg Glu Glu Val Ala
65                  70                  75                  80

Leu Lys Ile Asn Leu Pro Glu Ser Arg Val Gln Val Trp Phe Lys Asn
                85                  90                  95

Arg Arg Ala Lys Cys Arg Gln Gln Gln Gln Gln Gln Gln Asn Gly Gly
            100                 105                 110

Gln Asn Lys Val Arg Pro Ala Lys Lys Lys Thr Ser Pro Ala Arg Glu
        115                 120                 125

Val Ser Ser Glu Ser Gly Thr Ser Gly Gln Phe Thr Pro Pro Ser Ser
130                 135                 140

Thr Ser Val Pro Thr Ile Ala Ser Ser Ala Pro Val Ser Ile Trp
145                 150                 155                 160

Ser Pro Ala Ser Ile Ser Pro Leu Ser Asp Pro Leu Ser Thr Ser Ser
                165                 170                 175

Ser Cys Met Gln Arg Ser Tyr Pro Met Thr Tyr Thr Gln Ala Ser Gly
            180                 185                 190

Tyr Ser Gln Gly Tyr Ala Gly Ser Thr Ser Tyr Phe Gly Gly Met Asp
        195                 200                 205

Cys Gly Ser Tyr Leu Thr Pro Met His His Gln Glu Pro Gly Pro Gly
210                 215                 220

Ala Thr Leu Ser Pro Met Gly Thr Asn Ala Val Thr Ser His Leu Asn
225                 230                 235                 240

Gln Ser Pro Ala Ser Leu Ser Thr Gln Gly Tyr Gly Ala Ser Ser Leu
                245                 250                 255

Gly Phe Asn Ser Thr Thr Asp Cys Leu Asp Tyr Lys Asp Gln Thr Ala
            260                 265                 270

Ser Trp Lys Leu Asn Phe Asn Ala Asp Cys Leu Asp Tyr Lys Asp Gln
        275                 280                 285

Thr Ser Ser Trp Lys Phe Gln Val Leu
        290                 295

<210> SEQ ID NO 11
<211> LENGTH: 297
<212> TYPE: PRT
```

<213> ORGANISM: Artificial Sequence
<220> FEATURE:
<223> OTHER INFORMATION: OTX2 (F258E)

<400> SEQUENCE: 11

```
Met Met Ser Tyr Leu Lys Gln Pro Pro Tyr Ala Val Asn Gly Leu Ser
1               5                   10                  15

Leu Thr Thr Ser Gly Met Asp Leu Leu His Pro Ser Val Gly Tyr Pro
            20                  25                  30

Gly Pro Trp Ala Ser Cys Pro Ala Ala Thr Pro Arg Lys Gln Arg Arg
        35                  40                  45

Glu Arg Thr Thr Phe Thr Arg Ala Gln Leu Asp Val Leu Glu Ala Leu
50                  55                  60

Phe Ala Lys Thr Arg Tyr Pro Asp Ile Phe Met Arg Glu Glu Val Ala
65                  70                  75                  80

Leu Lys Ile Asn Leu Pro Glu Ser Arg Val Gln Val Trp Phe Lys Asn
                85                  90                  95

Arg Arg Ala Lys Cys Arg Gln Gln Gln Gln Gln Gln Asn Gly Gly
            100                 105                 110

Gln Asn Lys Val Arg Pro Ala Lys Lys Lys Thr Ser Pro Ala Arg Glu
        115                 120                 125

Val Ser Ser Glu Ser Gly Thr Ser Gly Gln Phe Thr Pro Pro Ser Ser
    130                 135                 140

Thr Ser Val Pro Thr Ile Ala Ser Ser Ala Pro Val Ser Ile Trp
145                 150                 155                 160

Ser Pro Ala Ser Ile Ser Pro Leu Ser Asp Pro Leu Ser Thr Ser Ser
                165                 170                 175

Ser Cys Met Gln Arg Ser Tyr Pro Met Thr Tyr Thr Gln Ala Ser Gly
            180                 185                 190

Tyr Ser Gln Gly Tyr Ala Gly Ser Thr Ser Tyr Phe Gly Gly Met Asp
        195                 200                 205

Cys Gly Ser Tyr Leu Thr Pro Met His His Gln Leu Pro Gly Pro Gly
    210                 215                 220

Ala Thr Leu Ser Pro Met Gly Thr Asn Ala Val Thr Ser His Leu Asn
225                 230                 235                 240

Gln Ser Pro Ala Ser Leu Ser Thr Gln Gly Tyr Gly Ala Ser Ser Leu
                245                 250                 255

Gly Glu Asn Ser Thr Thr Asp Cys Leu Asp Tyr Lys Asp Gln Thr Ala
            260                 265                 270

Ser Trp Lys Leu Asn Phe Asn Ala Asp Cys Leu Asp Tyr Lys Asp Gln
        275                 280                 285

Thr Ser Ser Trp Lys Phe Gln Val Leu
    290                 295
```

<210> SEQ ID NO 12
<211> LENGTH: 422
<212> TYPE: PRT
<213> ORGANISM: Artificial Sequence
<220> FEATURE:
<223> OTHER INFORMATION: PAX6 (L130E)

<400> SEQUENCE: 12

```
Met Gln Asn Ser His Ser Gly Val Asn Gln Leu Gly Gly Val Phe Val
1               5                   10                  15

Asn Gly Arg Pro Leu Pro Asp Ser Thr Arg Gln Lys Ile Val Glu Leu
            20                  25                  30
```

Ala His Ser Gly Ala Arg Pro Cys Asp Ile Ser Arg Ile Leu Gln Val
            35                  40                  45

Ser Asn Gly Cys Val Ser Lys Ile Leu Gly Arg Tyr Tyr Glu Thr Gly
 50                  55                  60

Ser Ile Arg Pro Arg Ala Ile Gly Gly Ser Lys Pro Arg Val Ala Thr
65                  70                  75                  80

Pro Glu Val Val Ser Lys Ile Ala Gln Tyr Lys Arg Glu Cys Pro Ser
                85                  90                  95

Ile Phe Ala Trp Glu Ile Arg Asp Arg Leu Leu Ser Glu Gly Val Cys
            100                 105                 110

Thr Asn Asp Asn Ile Pro Ser Val Ser Ser Ile Asn Arg Val Leu Arg
            115                 120                 125

Asn Glu Ala Ser Glu Lys Gln Gln Met Gly Ala Asp Gly Met Tyr Asp
130                 135                 140

Lys Leu Arg Met Leu Asn Gly Gln Thr Gly Ser Trp Gly Thr Arg Pro
145                 150                 155                 160

Gly Trp Tyr Pro Gly Thr Ser Val Pro Gly Gln Pro Thr Gln Asp Gly
                165                 170                 175

Cys Gln Gln Gln Glu Gly Gly Gly Glu Asn Thr Asn Ser Ile Ser Ser
            180                 185                 190

Asn Gly Glu Asp Ser Asp Glu Ala Gln Met Arg Leu Gln Leu Lys Arg
            195                 200                 205

Lys Leu Gln Arg Asn Arg Thr Ser Phe Thr Gln Glu Gln Ile Glu Ala
210                 215                 220

Leu Glu Lys Glu Phe Glu Arg Thr His Tyr Pro Asp Val Phe Ala Arg
225                 230                 235                 240

Glu Arg Leu Ala Ala Lys Ile Asp Leu Pro Glu Ala Arg Ile Gln Val
                245                 250                 255

Trp Phe Ser Asn Arg Arg Ala Lys Trp Arg Arg Glu Glu Lys Leu Arg
            260                 265                 270

Asn Gln Arg Arg Gln Ala Ser Asn Thr Pro Ser His Ile Pro Ile Ser
            275                 280                 285

Ser Ser Phe Ser Thr Ser Val Tyr Gln Pro Ile Pro Gln Pro Thr Thr
290                 295                 300

Pro Val Ser Ser Phe Thr Ser Gly Ser Met Leu Gly Arg Thr Asp Thr
305                 310                 315                 320

Ala Leu Thr Asn Thr Tyr Ser Ala Leu Pro Pro Met Pro Ser Phe Thr
                325                 330                 335

Met Ala Asn Asn Leu Pro Met Gln Pro Pro Val Pro Ser Gln Thr Ser
            340                 345                 350

Ser Tyr Ser Cys Met Leu Pro Thr Ser Pro Ser Val Asn Gly Arg Ser
            355                 360                 365

Tyr Asp Thr Tyr Thr Pro Pro His Met Gln Thr His Met Asn Ser Gln
370                 375                 380

Pro Met Gly Thr Ser Gly Thr Thr Ser Thr Gly Leu Ile Ser Pro Gly
385                 390                 395                 400

Val Ser Val Pro Val Gln Val Pro Gly Ser Glu Pro Asp Met Ser Gln
                405                 410                 415

Tyr Trp Pro Arg Leu Gln
            420

<210> SEQ ID NO 13
<211> LENGTH: 336
<212> TYPE: PRT

<213> ORGANISM: Artificial Sequence
<220> FEATURE:
<223> OTHER INFORMATION: VAX1 (L305E)

<400> SEQUENCE: 13

```
Met Phe Gly Lys Thr Asp Lys Met Asp Val Arg Cys His Ser Asp Thr
1               5                   10                  15

Glu Ala Ala Arg Val Ser Lys Asn Ala His Lys Glu Ser Arg Glu Ile
            20                  25                  30

Lys Gly Ala Glu Gly Ser Leu Pro Ala Ala Phe Leu Lys Glu Pro Gln
        35                  40                  45

Gly Ala Phe Ser Ala Ser Gly Ala Ser Glu Asp Cys Asn Lys Ser Lys
    50                  55                  60

Ser Asn Ser Ser Ala Asp Pro Asp Tyr Cys Arg Arg Ile Leu Val Arg
65                  70                  75                  80

Asp Ala Lys Gly Ser Ile Arg Glu Ile Ile Leu Pro Lys Gly Leu Asp
                85                  90                  95

Leu Asp Arg Pro Lys Arg Thr Arg Thr Ser Phe Thr Ala Glu Gln Leu
            100                 105                 110

Tyr Arg Leu Glu Met Glu Phe Gln Arg Cys Gln Tyr Val Val Gly Arg
        115                 120                 125

Glu Arg Thr Glu Leu Ala Arg Gln Leu Asn Leu Ser Glu Thr Gln Val
    130                 135                 140

Lys Val Trp Phe Gln Asn Arg Arg Thr Lys Gln Lys Asp Gln Gly
145                 150                 155                 160

Lys Asp Ser Glu Leu Arg Ser Val Val Ser Glu Thr Ala Ala Thr Cys
                165                 170                 175

Ser Val Leu Arg Leu Leu Glu Gln Gly Arg Leu Leu Ser Pro Pro Gly
            180                 185                 190

Leu Pro Ala Leu Leu Pro Pro Cys Ala Thr Gly Ala Leu Gly Ser Ala
        195                 200                 205

Leu Arg Gly Pro Ser Leu Pro Ala Leu Gly Ala Gly Ala Ala Ala Gly
    210                 215                 220

Ser Ala Ala Ala Ala Ala Ala Ala Thr Ala Pro Gly Pro Ala Gly
225                 230                 235                 240

Ala Ala Ser Gln His Pro Pro Ala Val Gly Gly Ala Pro Gly Pro Gly
                245                 250                 255

Pro Ala Gly Pro Gly Gly Leu His Ala Gly Ala Pro Thr Ala Ser His
            260                 265                 270

Gly Leu Phe Ser Leu Pro Val Pro Ser Leu Leu Gly Ser Val Ala Ser
        275                 280                 285

Arg Leu Ser Ser Ala Pro Leu Thr Met Ala Gly Ser Leu Ala Gly Asn
    290                 295                 300

Glu Gln Glu Leu Ser Ala Arg Tyr Leu Ser Ser Ser Ala Phe Glu Pro
305                 310                 315                 320

Tyr Ser Arg Thr Asn Asn Lys Glu Gly Ala Glu Lys Lys Ala Leu Asp
                325                 330                 335
```

METHOD FOR REGULATING SECRETION ABILITY OF HOMEOPROTEINS AND THEIR VARIANTS HAVING ALTERED SECRETION ABILITY

CROSS-REFERENCE TO RELATED APPLICATION

This application claims priority to Korean Patent Application No. 10-2019-0159210 (filed on Dec. 3, 2019), which is hereby incorporated by reference in its entirety.

BACKGROUND

The present invention relates to a method for regulating the extracellular secretion ability of a homeoprotein and a homeoprotein variant having regulated extracellular secretion ability using the same, and more particularly, to a method for increasing or decreasing the extracellular secretion ability through the increase or decrease in hydrophobicity of a homeodomain external amino acid sequence, or a homeoprotein whose extracellular secretion ability is increased or decreased through the increase or decrease in hydrophobicity of the homeodomain external amino acid sequence.

Since cells are surrounded by a hydrophobic cell membrane, hydrophilic biopolymers such as proteins and nucleic acids produced inside the cell cannot pass through the cell membrane and can act while staying only inside the cell. However, proteins which act by being secreted outside the cell, such as growth hormones, are secreted outside the cell via organelles that secrete intracellular proteins, including the endoplasmic reticulum and Golgi apparatus. Proteins which can migrate by the above secretory pathway have a specific secretory label, but most proteins do not have this label, and thus are produced inside the cell and disappear after completing their functions.

A transcription factor is present by moving to the nucleus of a cell where target DNA is located to perform an original function of inducing the transcription process which produces RNA by decoding the genetic information included in a DNA sequence, and since RNA produced through transcription induces the formation of proteins responsible for various intracellular reactions through the translation process, the presence or absence of transcription factors which induce the transcription of specific RNA has an important meaning for defining the characteristics of the corresponding cell. Therefore, the characteristics of the corresponding cell may be completely determined only when the transcription factor is produced, acts, and disappears.

Among transcription factors, homeoproteins, which are known to be particularly important for determining cell fate during development, are known to have various intracellular functions in addition to typical transcriptional regulatory functions. In particular, the characteristics that regulate the process of translating cytoplasmic RNA into a protein have been found to be important in determining the head and body of a Drosphilia early embryo.

Meanwhile, a foreign homeoprotein is introduced through the cell membrane, and such cell membrane-penetrating function was first found by French researchers in 1991. To date, it has been confirmed that intercellular protein transfer is possible among about 10 types of homeoproteins, and although research on the introduction of proteins using the homeodomain of human homeoproteins has been conducted (Korean Patent No. 10-1106262), research has been insufficiently conducted on the effects of amino acid sequences outside the homeodomain on the external secretion of homeoproteins.

SUMMARY

The present inventors have first elucidated that the presence or absence of a hydrophobic amino acid sequence outside the homeodomain as well as the homeodomain itself are associated with the factors which affect the extracellular secretion ability of homeoproteins, and confirmed that the extracellular secretion ability is decreased in cultured cells and in vivo tissues by substituting the hydrophobic amino acid sequence with a hydrophilic amino acid sequence, and in contrast, homeoproteins with increased extracellular secretion ability in cultured cells and in vivo tissues could be induced by substituting a hydrophilic amino acid sequence at the corresponding position with the hydrophobic amino acid sequence, thereby completing the present invention based on this.

Thus, an object of the present invention is to provide a homeoprotein variant whose extracellular secretion ability is increased and decreased, which is selected from the group consisting of the following variants:

1) a variant in which amino acid 233 of a HOXD4 protein consisting of an amino acid sequence represented by SEQ ID NO: 1 has been substituted;

2) a variant in which amino acid 305 of a SHOX2 protein consisting of an amino acid sequence represented by SEQ ID NO: 2 has been substituted;

3) a variant in which amino acids 143 and 191 of an EN2 protein consisting of an amino acid sequence represented by SEQ ID NO: 3 have been substituted;

4) a variant in which amino acid 220 or 258 of an OTX2 protein consisting of an amino acid sequence represented by SEQ ID NO: 4 has been substituted;

5) a variant in which amino acid 130 of a PAX6 protein consisting of an amino acid sequence represented by SEQ ID NO: 5 has been substituted; and 6) a variant in which amino acid 305 of a VAX1 protein consisting of an amino acid sequence represented by SEQ ID NO: 6 has been substituted.

Further, another object of the present invention is to provide a method for increasing or decreasing the extracellular secretion ability of a homeoprotein or a method for producing a homeoprotein whose extracellular secretion ability is increased or decreased, the method including substituting one amino acid selected from the group consisting of the following groups.

In addition, still another object of the present invention is to provide a method for predicting the extracellular secretion ability of a homeoprotein, the method including confirming one amino acid from the group consisting of the following amino acids:

1) amino acid 233 of a HOXD4 protein, consisting of an amino acid sequence represented by SEQ ID NO: 1;

2) amino acid 305 of a SHOX2 protein, consisting of an amino acid sequence represented by SEQ ID NO: 2;

3) amino acids 143 and 191 of an EN2 protein, consisting of an amino acid sequence represented by SEQ ID NO: 3;

4) amino acid 220 or 258 of an OTX2 protein, consisting of an amino acid sequence represented by SEQ ID NO: 4;

5) amino acid 130 of a PAX6 protein, consisting of an amino acid sequence represented by SEQ ID NO: 5; and 6) amino acid 305 of a VAX1 protein, consisting of an amino acid sequence represented by SEQ ID NO: 6.

However, a technical problem to be achieved by the present invention is not limited to the aforementioned problem, and the other problems that are not mentioned may be clearly understood by a person skilled in the art from the following description.

To achieve the objects of the present invention as described above, the present invention provides a homeoprotein variant whose extracellular secretion ability is increased or decreased, which is selected from the group consisting of the following variants:

1) a variant in which amino acid 233 of a HOXD4 protein consisting of an amino acid sequence represented by SEQ ID NO: 1 has been substituted;

2) a variant in which amino acid 305 of a SHOX2 protein consisting of an amino acid sequence represented by SEQ ID NO: 2 has been substituted;

3) a variant in which amino acids 143 and 191 of an EN2 protein consisting of an amino acid sequence represented by SEQ ID NO: 3 have been substituted;

4) a variant in which amino acid 220 or 258 of an OTX2 protein consisting of an amino acid sequence represented by SEQ ID NO: 4 has been substituted;

5) a variant in which amino acid 130 of a PAX6 protein consisting of an amino acid sequence represented by SEQ ID NO: 5 has been substituted; and 6) a variant in which amino acid 305 of a VAX1 protein consisting of an amino acid sequence represented by SEQ ID NO: 6 has been substituted.

As an exemplary embodiment of the present invention, the amino acids may be an amino acid within an external motif of a homeodomain.

As another exemplary embodiment of the present invention, when the amino acid is substituted with a hydrophobic amino acid, the extracellular secretion ability may be increased.

As still another exemplary embodiment of the present invention, the hydrophobic amino acid may be leucine (Leu)(L).

As yet another exemplary embodiment of the present invention, when the amino acid is substituted with a hydrophilic amino acid, the extracellular secretion ability may be decreased.

As yet another object of the present invention, the hydrophilic amino acid may be glutamate (Glu)(E).

In addition, the present invention provides a method for increasing or decreasing the extracellular secretion ability of a homeoprotein or a method for producing a homeoprotein whose extracellular secretion ability is increased or decreased, the method including substituting one amino acid selected from the group consisting of the following groups.

Furthermore, the present invention provides a method for predicting the extracellular secretion ability of a homeoprotein, the method including confirming one amino acid selected from the group consisting of the following amino acids:

1) amino acid 233 of a HOXD4 protein, consisting of an amino acid sequence represented by SEQ ID NO: 1;

2) amino acid 305 of a SHOX2 protein, consisting of an amino acid sequence represented by SEQ ID NO: 2;

3) amino acids 143 and 191 of an EN2 protein, consisting of an amino acid sequence represented by SEQ ID NO: 3;

4) amino acid 220 or 258 of an OTX2 protein, consisting of an amino acid sequence represented by SEQ ID NO: 4;

5) amino acid 130 of a PAX6 protein, consisting of an amino acid sequence represented by SEQ ID NO: 5; and 6) amino acid 305 of a VAX1 protein, consisting of an amino acid sequence represented by SEQ ID NO: 6.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which.

DETAILED DESCRIPTION

Figure 1:
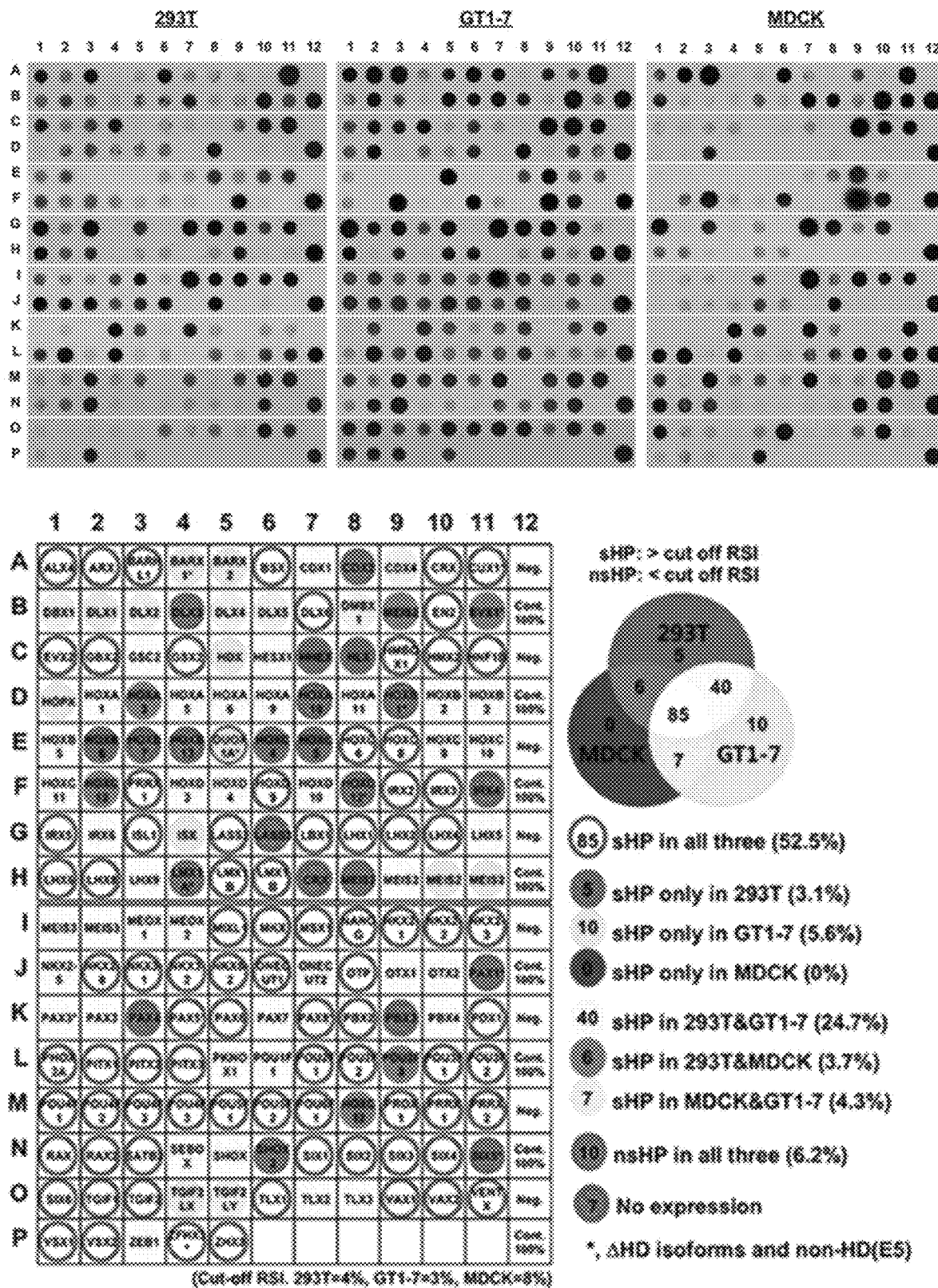
FIG. 1 illustrates images of V5-HP secretion of 293T, GT1-7 and MDCK cells in a medium (dot color indicates secretion observed in the corresponding cell line)

Hereinafter, the present invention will be described in detail.

The present inventors have first elucidated that the presence or absence of a hydrophobic amino acid sequence outside the homeodomain as well as the homeodomain itself are associated with the factors which affect the extracellular secretion ability of homeoproteins, and confirmed that a homeoprotein whose extracellular secretion ability is increased or decreased could be induced through an increase or decrease in hydrophobicity of the amino acid sequence, thereby completing the present invention based on this.

As used herein, a homeodomain refers to a protein having a structure showing gene-binding activity and consisting of about 60 amino acids. The homeodomain is expressed from a gene having a size of 180 bp, which is known to be a homeobox. It is known that the homeodomain binds specifically to a target gene promotor site to promote or inhibit gene expression, the homeodomain is mainly identified in a protein group that regulates early Drosophila development, and is named as the homeodomain related to Drosophila development, and it is possible to find a group of segmental genes, genes which control the morphogenesis of vertebrate Hox genes and the like, a conjugation determinant gene MAT of yeast, transcription factor groups which control tissue-specific gene expression, and the like. Each of these groups of homeodomains has a characteristic amino acid alignment and exhibits evolutionary conservation in the animal kingdom. Proteins having a homeodomain are collectively referred to as homeoproteins, and in the present invention, the homeoprotein may be any one selected from the group consisting of HOXD4, SHOX2, EN2, OTX2, PAX6, and VAX1, but is not limited thereto.

As used herein, the external motif of the homeodomain refers to an amino acid sequence in a specific region out of the region of the homeodomain rather than the inside of the homeodomain, and the amino acid sequence fragment in the specific region may be located upstream or downstream of the homeodomain.

The present inventors specifically confirmed the correlation between the extracellular secretion ability of homeoproteins and the hydrophobic amino acids of the external motifs of homeodomains, and more specifically, an exemplary embodiment of the present invention confirmed that when leucine was substituted with glutamate at amino acid positions 143 and 191 of EN2 by performing an experiment of replacing a hydrophobic amino acid at each corresponding position of secretory homeodomain-containing proteins (sHP) with a hydrophilic amino acid glutamate (Glu)(E) in order to confirm the importance of hydrophobic residues in external motifs of homeodomains, the amount of mutant EN2 to be measured in growth media was reduced, and confirmed that the extracellular secretion ability of mutants in which leucine 220 of OTX, phenylalanine 258 of OTX, leucine 130 of PAX6, or leucine 305 of VAX1 had been changed to glutamate was reduced (see Example 3).

Further, another exemplary embodiment of the present invention confirmed that when a hydrophilic or hydrophobic amino acid sequence in the external motifs of homeodomains was substituted with a hydrophobic amino acid or another hydrophobic amino acid, and more specifically, the extracellular secretion ability of a mutant in which serine 233 of HOXD4 had been substituted with leucine or proline 305 of SHOX2 had been substituted with leucine was enhanced (see Example 3).

In addition, through still another exemplary embodiment of the present invention, it was confirmed that OTX2 (F258E) and PAX6 (L130E) still exhibited transcriptional activities, and luciferase reporter expression downstream of OTX2 target CRX promotor and tandem PAX6 binding sequences, respectively, as strong as wild-type OTX2 and PAX6 was induced, and it was confirmed that the hydrophobic residues were involved in the secretion of homeoproteins outside the cell without affecting the transcriptional activities of the sHPs by confirming that VAX1 (L305E) also activated the expression of luciferase, whose transcription was regulated by a VAX1 target transcription factor 7-like 2 (TCF7L2) gene upstream sequence, as significantly as wild-type VAX1 (see Example 5).

Through the experimental results of the exemplary embodiments, the present inventors suggest that when a specific hydrophobic amino acid of the external motifs of homeodomains of a homeoprotein is substituted with a hydrophilic amino acid, only the extracellular secretion ability of the homeoprotein can be reduced without reducing the transcriptional activities of the homeoprotein.

Thus, the present invention provides a homeoprotein variant whose extracellular secretion ability is increased or decreased, which is selected from the group consisting of the following variants:

1) a variant in which amino acid 233 of a HOXD4 protein consisting of an amino acid sequence represented by SEQ ID NO: 1 has been substituted;

2) a variant in which amino acid 305 of a SHOX2 protein consisting of an amino acid sequence represented by SEQ ID NO: 2 has been substituted;

3) a variant in which amino acids 143 and 191 of an EN2 protein consisting of an amino acid sequence represented by SEQ ID NO: 3 have been substituted;

4) a variant in which amino acid 220 or 258 of an OTX2 protein consisting of an amino acid sequence represented by SEQ ID NO: 4 has been substituted;

5) a variant in which amino acid 130 of a PAX6 protein consisting of an amino acid sequence represented by SEQ ID NO: 5 has been substituted; and 6) a variant in which amino acid 305 of a VAX1 protein consisting of an amino acid sequence represented by SEQ ID NO: 6 has been substituted.

The amino acid according to the present invention may be an amino acid in the external motifs of homeodomains, and when the amino acid according to the present invention is substituted with a hydrophobic amino acid, the extracellular secretion ability may be enhanced, and the hydrophobic amino acid may be leucine (Leu)(L), but is not limited thereto.

In the present invention, a hydrophobic amino acid is a general term for amino acids which strongly tend to be present inside proteins in an aqueous solution, and more specifically, examples of the hydrophobic amino acid include phenylalanine, tryptophan, isoleucine, leucine, proline, methionine, valine, glycine, alanine, cysteine, and the like. The conformation of the protein is supported by hydrophobic interactions between hydrophobic residues. In addition, there is a hydrophobic amino acid which forms a part of the substrate binding site at the enzyme active center site. Hydrophobic amino acids other than proline also have a great ability to form β structures. A hydrophobic region of the protein surface is considered to be a place where the protein surface binds to other proteins, lipid parts of biological membranes, or hydrophobic ligands.

The amino acid according to the present invention may be an amino acid in the external motifs of homeodomains, and when the amino acid according to the present invention is substituted with a hydrophilic amino acid, the extracellular secretion ability may be reduced, and the hydrophilic amino acid may be glutamate (Glu)(E), but is not limited thereto.

In addition, as another aspect of the present invention, the present invention provides a method for increasing or decreasing the extracellular secretion ability of a homeoprotein or a method for producing a homeoprotein whose extracellular secretion ability is increased or decreased, the method including substituting one amino acid selected from the group consisting of the following amino acids:

1) amino acid 233 of a HOXD4 protein, consisting of an amino acid sequence represented by SEQ ID NO: 1;
2) amino acid 305 of a SHOX2 protein, consisting of an amino acid sequence represented by SEQ ID NO: 2;
3) amino acids 143 and 191 of an EN2 protein, consisting of an amino acid sequence represented by SEQ ID NO: 3;
4) amino acid 220 or 258 of an OTX2 protein, consisting of an amino acid sequence represented by SEQ ID NO: 4;
5) amino acid 130 of a PAX6 protein, consisting of an amino acid sequence represented by SEQ ID NO: 5; and
6) amino acid 305 of a VAX1 protein, consisting of an amino acid sequence represented by SEQ ID NO: 6.

Furthermore, as still another aspect of the present invention, the present invention provides a method for predicting the extracellular secretion ability of a homeoprotein, the method including confirming one amino acid selected from the group consisting of the following amino acids:

1) amino acid 233 of a HOXD4 protein, consisting of an amino acid sequence represented by SEQ ID NO: 1;
2) amino acid 305 of a SHOX2 protein, consisting of an amino acid sequence represented by SEQ ID NO: 2;
3) amino acids 143 and 191 of an EN2 protein, consisting of an amino acid sequence represented by SEQ ID NO: 3;
4) amino acid 220 or 258 of an OTX2 protein, consisting of an amino acid sequence represented by SEQ ID NO: 4;
5) amino acid 130 of a PAX6 protein, consisting of an amino acid sequence represented by SEQ ID NO: 5; and 6) amino acid 305 of a VAX1 protein, consisting of an amino acid sequence represented by SEQ ID NO: 6.

Hereinafter, preferred examples for helping the understanding of the present invention will be suggested. However, the following examples are provided only to more easily understand the present invention, and the contents of the present invention are not limited by the following examples.

EXAMPLES

Example 1

Experimental Preparation and Experimental Methods 1-1. Animal

All experiments done with the mice were performed according to approved Institutional Animal Care and Use Committee (IACUC) protocols (KAIST IACUC 13-130) of Korea Advanced Institute of Science and Technology (KAIST).

1-2. Gateway Cloning of Human HP ORFs 170 human HP cDNAs were obtained from human ORFeome v7.0 developed by the Dana-Farber Cancer Research Institute (DFCRI) and human ORFeome developed by Johns Hopkins University, and the HP ORFs were cloned into a pCAGIG-V5 vector using Gateway cloning technology (Invitrogen) for expression in cultured cell-lines and mouse embryonic brains.

1-3. Cell Culture, Transfection, and Dot Blot Analysis

293T, HeLa, GT1-7, and MDCK cells were maintained in Dulbecco's modified Eagle medium (DMEM) containing 10% fetal bovine serum (FBS). 293T cells were then transfected with polyethylenimine (PEI), and HeLa, GT1-7, and MDCK cells were transfected using the GenJet plus DNA in vitro transfection reagent (Signagen) following the manufacturer's manual. The growth media of the transfected cells were replaced with FreeStyle serum-free media (GIBCO BRL) 6 hours after transfection, and were collected. 500 ml of the media were added into each well of the GE Whatman Dot-Blot 96 Well Plate System, which was applied under vacuum to aspirate the media across the PVDF membrane. The membranes, which captured proteins and nucleic acids in the growth media, were then blotted with anti-V5 and anti-GFP antibodies, simultaneously, the transfected cells were lysed in RIPA buffer (PBS with 0.1% SDS), and supernatants were collected for western blot analyses.

1-4. Immunostaining

Mouse embryonic brains and eyes were isolated for subsequent fixation in PBS containing 4% paraformaldehyde (PFA) for 1 hour. The samples were then moved into 20% sucrose/PBS solution for subsequent incubation at 4° C. for 16 hours prior to cryopreservation in the TissueTek O.C.T. compound for freezing.

Frozen samples having a thickness between 12 mm and 20 mm were then cryosectioned onto a slide glass. Alternatively, HeLa cells cultured on the coverslips were fixed in 4% PFA/PBS for 20 minutes. The tissues on the slides and HeLa cells on the coverslips were then incubated in a blocking solution (PBS including 10% normal donkey serum and 0.1% Triton X-100) at room temperature for 1 hour. The cells were further incubated in a blocking solution including primary antibodies without Triton X-100 at 4° C. for 16 hours, and subsequently with fluorophore-conjugated secondary antibodies recognizing the primary antibodies. Fluorescent images of the IHC signals were then obtained by the Olympus FV1000 confocal microscope.

1-5. Recombinant V5-HP Affinity Purification 293T cells expressing V5-tagged HP were lysed in a buffer consisting of 20 mM Tris-HCl (pH 7.9), 500 mM NaCl, 20% glycerol, 4 mM $MgCl_2$, 0.4 mM EDTA, and a protease inhibitor cocktail (Millipore). Supernatant fractions of the cells obtained after centrifugation at 13,200 rpm for 10 minutes were incubated with anti-V5 antibodies at 4° C. for 16 hours, and then with protein-G Sepharose (GE Healthcare) beads for 2 hours. The protein-G Sepharose immune complexes were washed five times with a wash buffer (20 mM Tris-HCl (pH 7.9), 150 mM NaCl, 2 mM $MgCl_2$, 0.2 mM EDTA, 0.1% NP40, and a protease inhibitor) before V5-tagged HPs. The protein-G Sepharose immune complexes were eluted from the protein-G Sepharose beads in the wash buffer containing 0.25 mg/ml V5 peptide. The V5 peptide was then removed by the Amicon Ultracentrifugal filter device (Millipore).

1-6. Retinal Explants and Axon Growth Analysis

Retinal explants were prepared as it was described in a previous report (Kim et al., 2014). Briefly, retinas were isolated from E13.5 mouse embryos and explants were added to a collagen mixture and positioned on plates coated with poly-L-lysine (10 μg/ml) and laminin (10 μg/ml). The explants were then incubated at 37° C. for 1 hour to allow gelling before adding a Neurobasal medium containing the B27 supplement (Invitrogen). The explants were cultured for 48 hours before being treated with proteins or co-cultured with 293T cell aggregates for 48 hours.

1-7. Quantification & Statistical Analysis

The multiple sequence alignment was then built by using Multiple Sequence Comparison by Log-Expectation (MUSCLE) software with the default option, which is designed to give the most accurate gapped alignment (Edgar, 2004). The multiple sequence alignment (MSA) results were split into two sub-MSAs for sHP and nsHP sequences with different RSI cut-offs, respectively, and the sequence profiles, which represent the amino acid frequencies in each MSA column, were calculated. To identify the distinctive MSA columns discriminating sHP and nsHP sequences, the difference between two sub-MSAs in MSA column i was calculated by using the JS-divergence defined as.

$$JSD_i(p, q) = \lambda \sum_{k=1}^{20} p_i(k) \log \frac{p_i(k)}{r_i(k)} + (1-\lambda) \sum_{k=1}^{20} q_i(k) \log \frac{q_i(k)}{r_i(k)}$$

where $p_i$ (k) and $q_i$ (k) represent the frequencies of the amino acid k in MSA column i in the sub-MSAs for sHP and nsHP sequences, respectively, and l is 0.5, and $r_i$ (k) is defined as $(p_i(k)+q_i(k))=2$.

1-8. Statistical Analysis

Statistical analysis was performed using Prism Software (GraphPad; v5.0) measurement tools. All statistical analysis data is expressed as the mean±STE. Comparison between two groups was done by an unpaired Student's t test, and the differences among multiple groups were determined by analysis of variance (ANOVA) with a Tukey's post-test used to determine the significant differences among multiple groups. P values<0.01 were considered as statistically significant results.

Example 2

Confirmation of Domains Affecting Extracellular Secretion of Homeoproteins

It has been suggested that the Sec motif, which is a linker region between the second and third helices of the homeodomain, is responsible for the secretion of En2, and as illustrated in FIG. 1, given that the Sec motif is shared by all HDs, it was confirmed there is no chance of or very little chance of secretion of HPX/HOPX, which has only a PRD class homeodomain without any other functional domain (RSI (293T): 0.00, RSI (GT1-7): 3.97, RSI (MDCK): 0.96).

Figure 2:
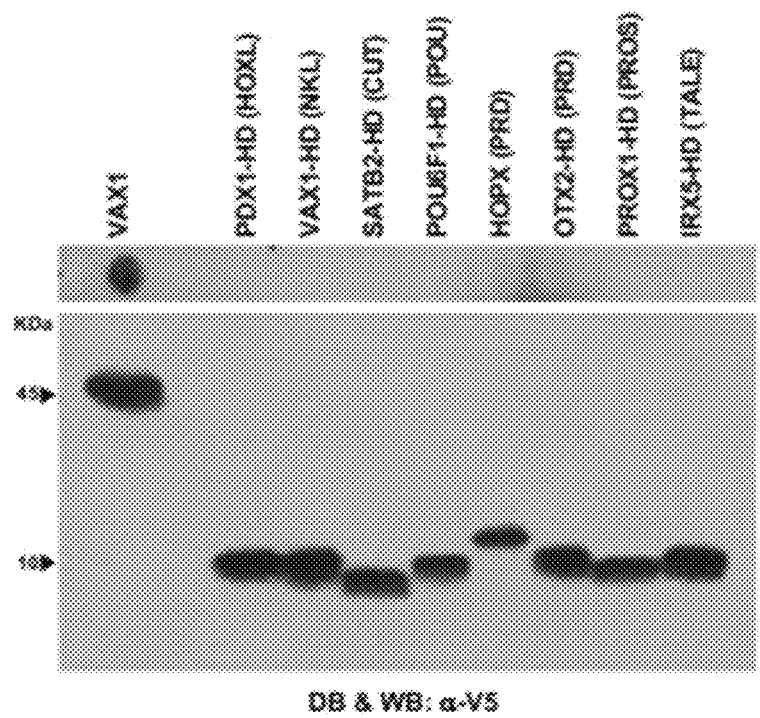
FIG. 2 illustrates the confirmation of the correlation between the homeodomain whose expression is observed in 293T cells and secretion by isolating the homeodomain from the homeoprotein.

Further, as illustrated in FIG. 2, as a result of further examining the secretabilities of various isolated homeodomains, no evidence of secretion was found in any of the three cell lines.

In contrast, as illustrated in FIG. 1, it was confirmed that the BARX1, EVX1, PAX3, and ZFHX3 isoforms lacking their homeodomains had an extracellular secretion ability even though there was no homeodomain in certain cell situations.

Figure 3:
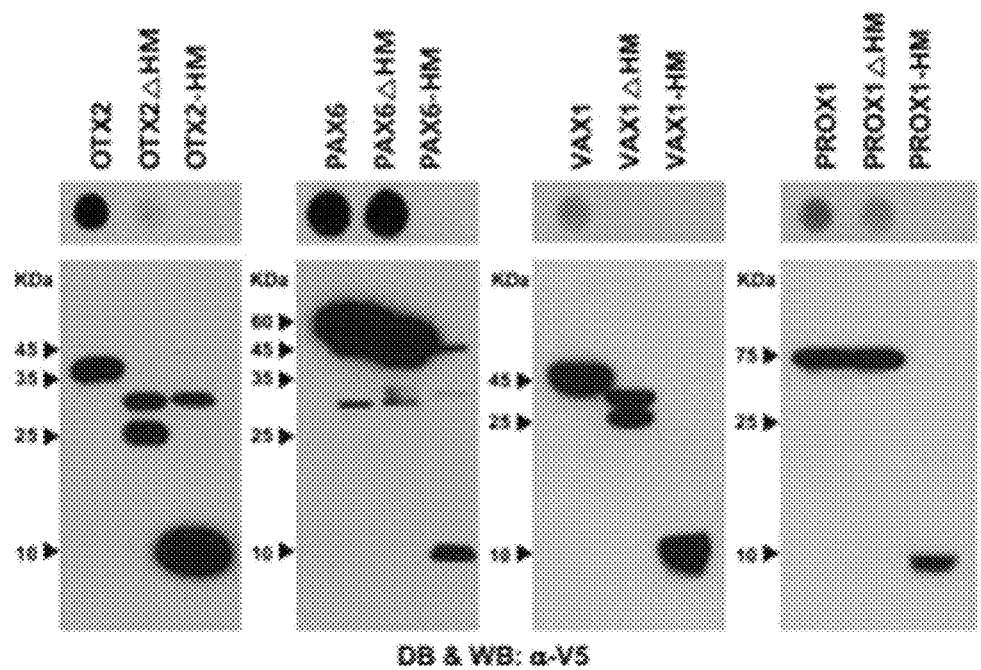
FIG. 3 illustrates the results of confirming the correlation between mutations of homeoproteins from which homeodomains have been deleted and secretion.

Thus, as a result of testing the secretion of secretory homeodomain-containing proteins (sHPs), as illustrated in FIG. 3, it was confirmed that OTX2 and PAX6 were still secreted without the homeodomain, whereas VAX1 should have its homeodomain for secretion.

Together, it can be confirmed that although the presence or absence of the homeodomain is an important requirement for the secretion of homeoproteins, it is not a sufficient requirement for the secretion of homeoproteins. In addition, it could be speculated that other domain motifs outside the homeodomain were required for extracellular secretion of homeoproteins.

Example 3

Figure 4:
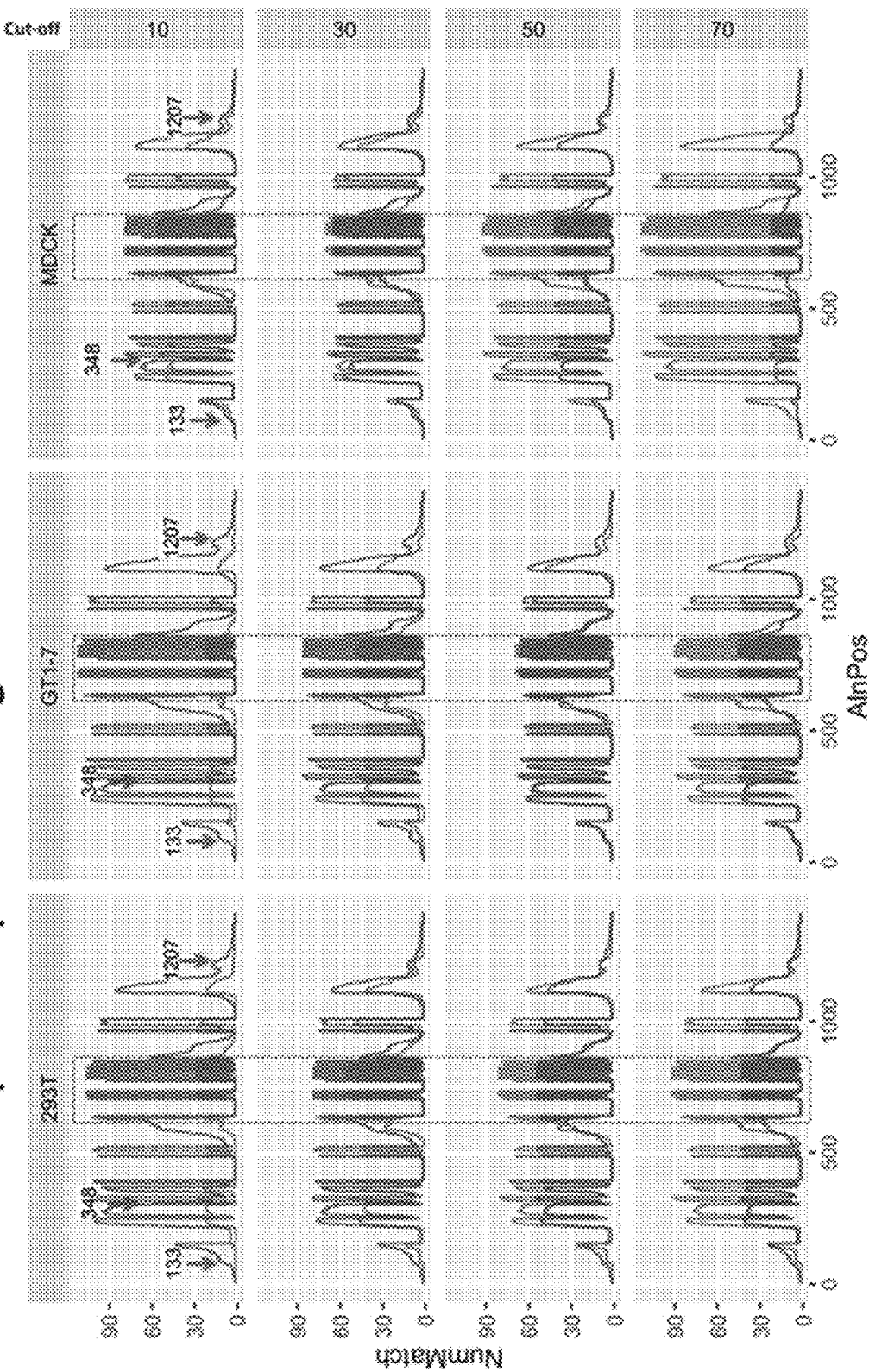
FIG. 4 illustrates the results of confirming shared motifs in sHPs using the multiple sequence alignment described in the STAR method.

Confirmation of Hydrophobic Amino Acid Sequence Affecting Extracellular Secretion of Homeoproteins Referring to the experimental results of Example 2, as illustrated in FIG. 4, it was tried to identify the motifs, which are located outside the homeodomain and are shared among various secretory homeodomain-containing proteins (sHPs), by multiple sequence alignment.

Figure 5:
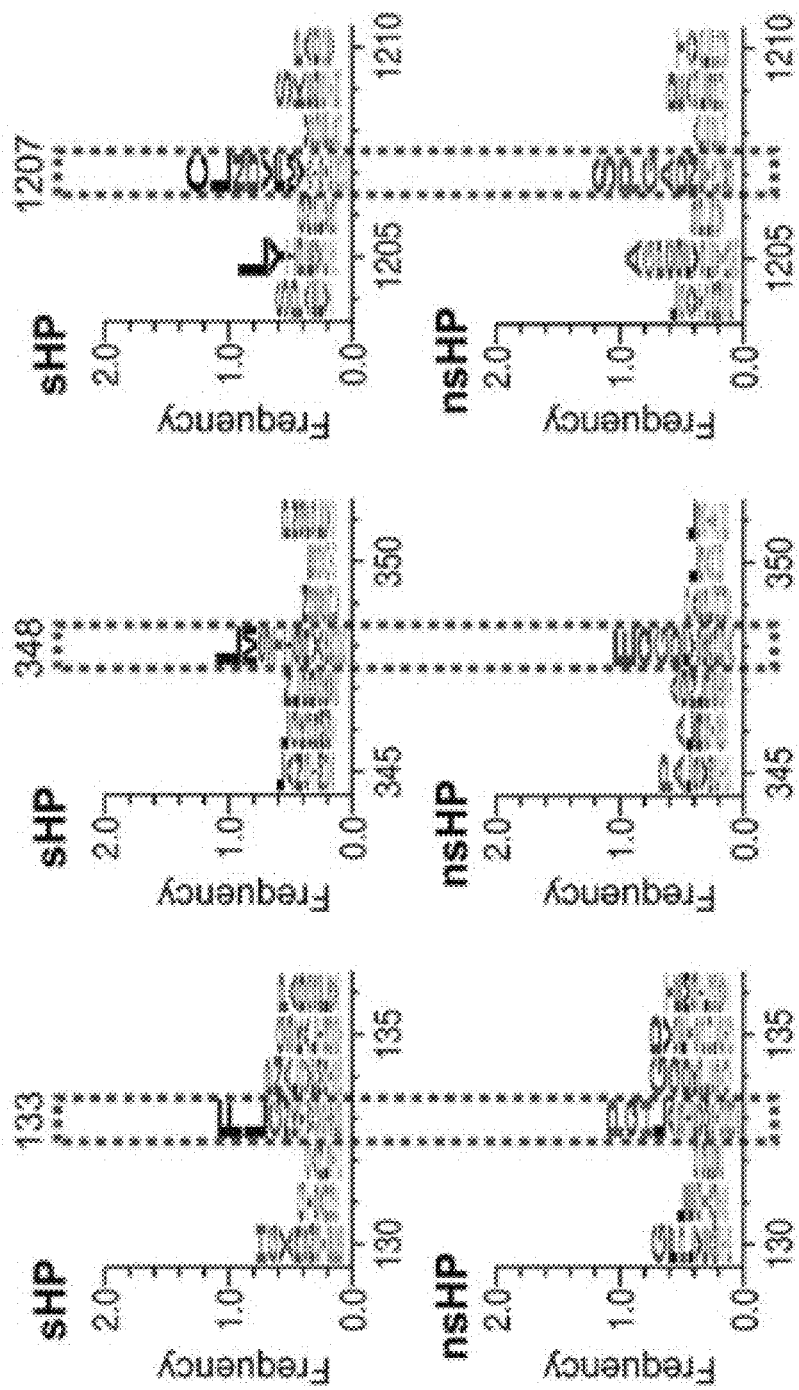
FIG. 5 illustrates the amino acid sequences of sHP and nsHP at the points indicated by the arrows in FIG. 4.

As a result, as illustrated in FIG. 5, it was confirmed that hydrophobic amino acids, including phenylalanine (Phe)(F), leucine (Leu)(L), and methionine (Met)(M), were commonly detectable at the same locations of the sHPs outside the homeodomain.

To confirm the importance of the residues in extracellular secretion of homeoproteins, an experiment of replacing amino acids at corresponding positions of secretory homeodomain-containing proteins (sHPs) with an acidic amino acid glutamate (Glu) was performed.

Figure 6:
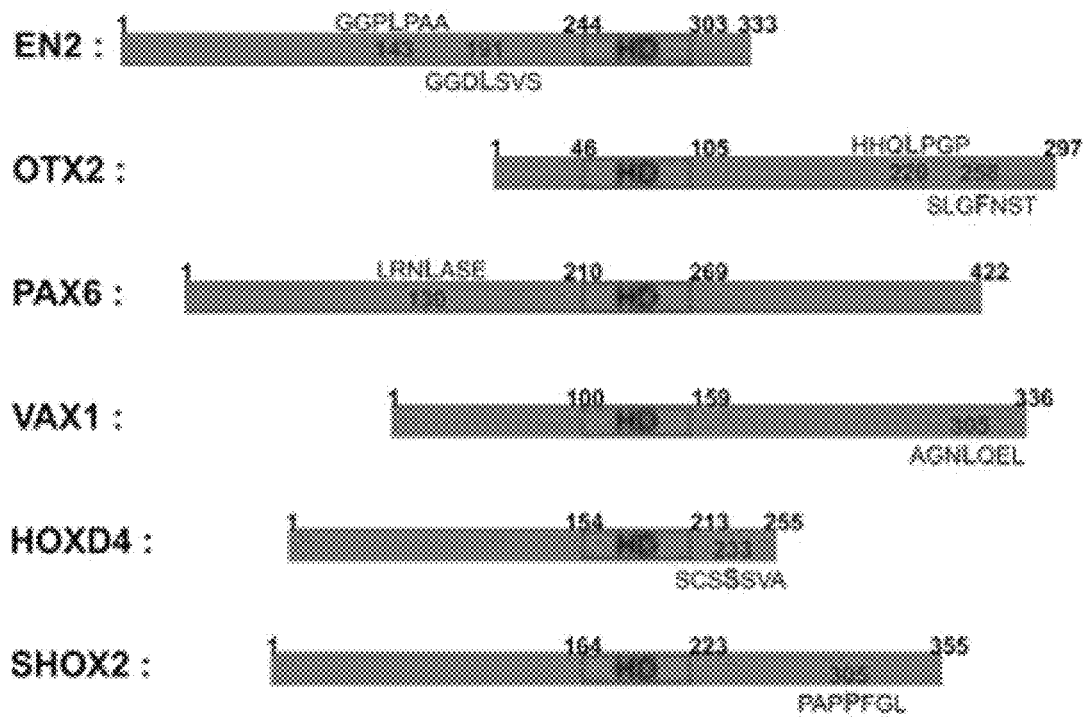
FIG. 6 illustrates the positions of amino acids which are expected to be shared by sHP and nsHP, respectively (homeodomains are colored in red)
Figure 7:
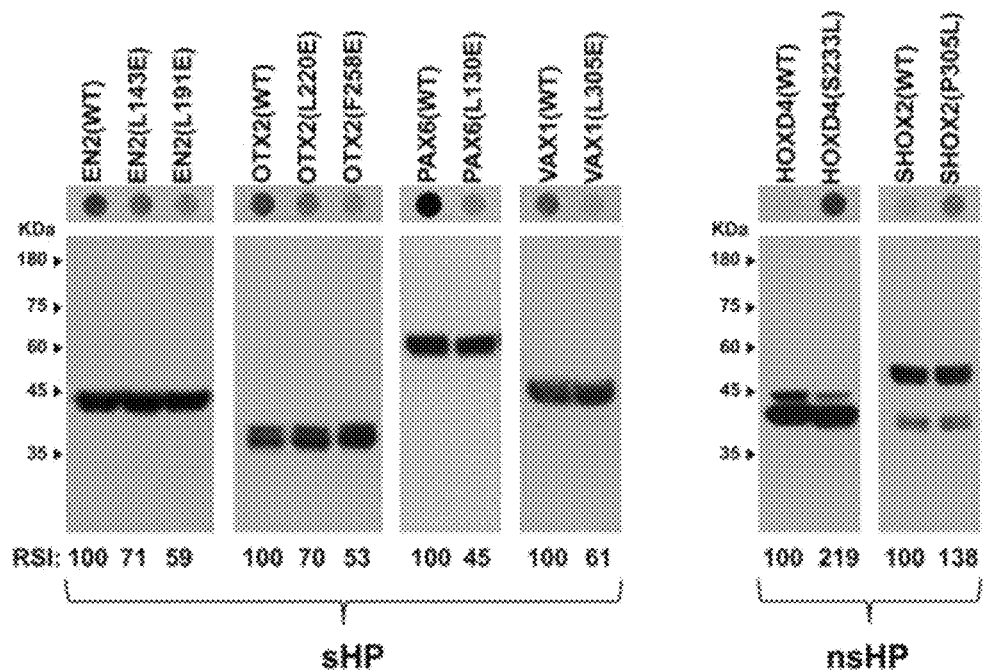
FIG. 7 illustrates a comparison of the extracellular secretion abilities of mutant homeoproteins (the scores below the image show the average relative secretion index (RSI) value compared with the secretion index of the wild-type homeoproteins)

As a result, as illustrated in FIGS. 6 and 7, it was confirmed that changing leucine (Leu)(L) residues at positions 143 and 191 of EN2 to glutamate (Glu)(E) reduced the amount of the secreted mutant EN2 measured in the growth media.

Together with the results, as illustrated in FIGS. 6 and 7, it was confirmed that the extracellular secretion ability of a mutant in which leucine (or phenylalanine) of other secretory homeodomain-containing proteins (sHPs) such as leucine 220 of OTX2, phenylalanine 258 of OTX2, leucine 130 of PAX6, and leucine 305 of VAX1 had been substituted with glutamate was reduced, and thus it could be seen that it is a general rule that the extracellular secretion ability of a homeoprotein in which leucine (or phenylalanine) had been substituted with glutamate was reduced. Here, each mutant is indicated as EN2 (L143E), EN2 (L191E), OTX2 (L220E), OTX2 (F258E), PAX6 (L130E), and VAX1 (L305E), respectively.

Conversely, as illustrated in FIGS. 6 and 7, it was confirmed that the extracellular secretion ability of a mutant in which serine 233 of HOXD4 was substituted with leucine or proline 305 of SHOX2 was substituted with leucine was enhanced in 293T cells. Here, each mutant is indicated as HOXD4 (S233L) and SHOX2 (P305L). The following Table 1 shows the sequence number of each mutant.

TABLE 1

| SEQ ID NO | Mutant |
|---|---|
| 7 | HOXD4 (S233L) |
| 8 | SHOX2 (P305L) |
| 9 | EN2 (L143E) EN2 (L191E) |
| 10 | OTX2 (L220E) |
| 11 | OTX2 (F258E) |
| 12 | PAX6 (L130E) |
| 13 | VAX1 (L305E) |

Example 4

Figure 8:
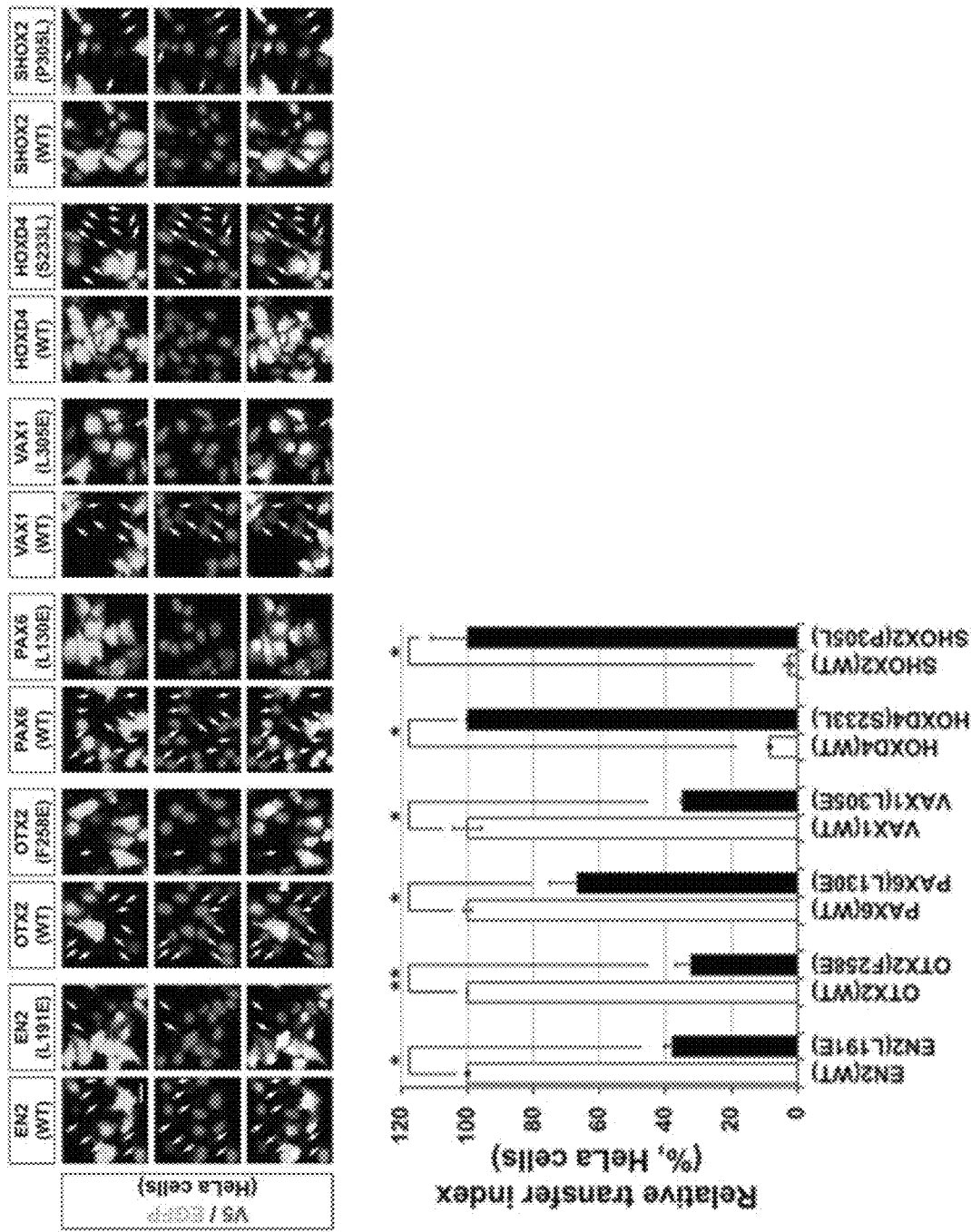
FIG. 8 illustrates images comparing the abilities of wild-type homeoproteins and mutant homeoproteins to be transferred between HeLa cells and relative transfer index (RTI) values ($*p<0.01$; $** p<0.005$; ANOVA., scale bars: 25 µm)

Confirmation of Correlation Between Extracellular Secretion Ability of Homeoproteins and Transfer Ability to Neighboring Cells As illustrated in FIG. 8, it was confirmed that in a mutant in which leucine (Leu)(L) residues at positions 143 and 191 of EN2 had been changed to glutamate (Glu)(E), a mutant in which leucine 220 of OTX2, phenylalanine 258 of OTX2, leucine 130 of PAX6, or leucine 305 of VAX1 had been substituted with glutamate, or secretory homeodomain-containing proteins (sHPs) defective in the cellular secretion ability, the efficiency of transfer between cells is reduced compared to wild-type homeoproteins.

Conversely, as illustrated in FIG. 8, it was confirmed that the transfer ability between HeLa cells of a mutant in which serine 233 of HOXD4 was substituted with leucine or proline 305 position of SHOX2 was substituted with leucine had been increased.

Figure 9:
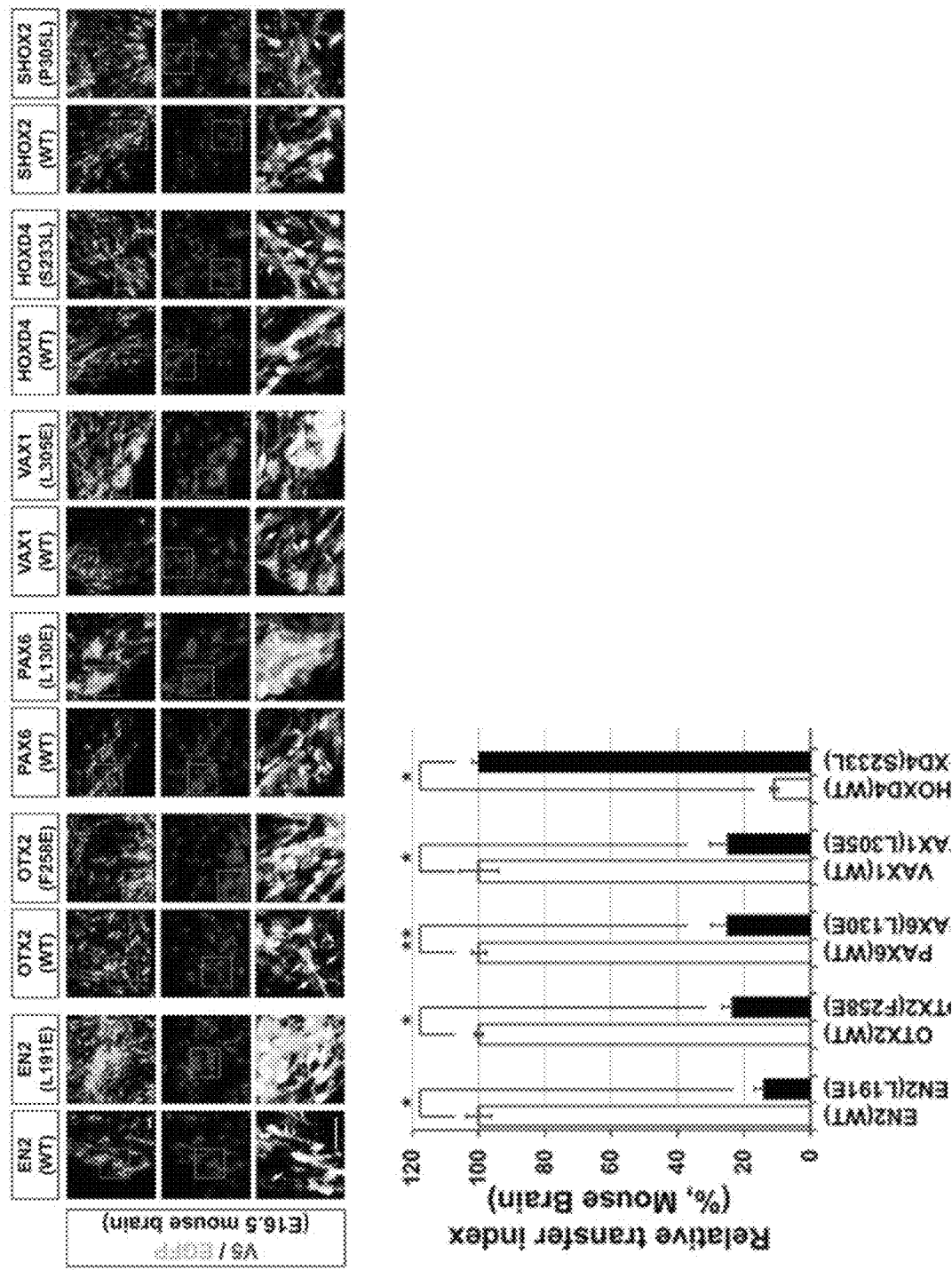
FIG. 9 illustrates images comparing the abilities of wild-type homeoproteins and mutant homeoproteins to be transferred between mouse embryonic brain cells and RTI values ($*p<0.01$; $** p<0.005$; ANOVA., scale bars: 25 µm)

Further, similar to the experimental results in the cultured cells, as illustrated in FIG. 9, it was confirmed that hydrophobic residues outside the homeodomain also played an important role for intercellular homeoprotein transfer in mouse brain cells.

When the results are combined, it is confirmed that rather than depending solely on the homeodomain, homeoprotein secretion is determined by each homeoprotein's three-dimensional structure, and the three-dimensional structure is determined by residues outside the homeodomain, such as the hydrophobic amino acids outside the homeodomain.

Furthermore, it is possible to predict that mutations or post-translational modifications at those sites can change the extracellular secretion ability of the homeoproteins.

Example 5

Confirmation of Correlation Between Extracellular Secretion Ability and Transcriptional Activity of Homeoproteins Through the above-described examples, it was confirmed that mutations in hydrophobic amino acid residues outside the homeodomain have a significant effect on homeoprotein secretion. Thus, the following experiments were conducted to confirm how the mutations affect the transcriptional activities of the homeoproteins.

As a result, as illustrated in FIGS. 8 and 9, it was confirmed that the mutation in which leucine or phenylalanine was substituted with glutamate among the amino acid residues outside the homeodomain did not change intracellular distribution of the sHPs, and all the mutant homeoproteins were detected in the nucleus.

Figure 10:
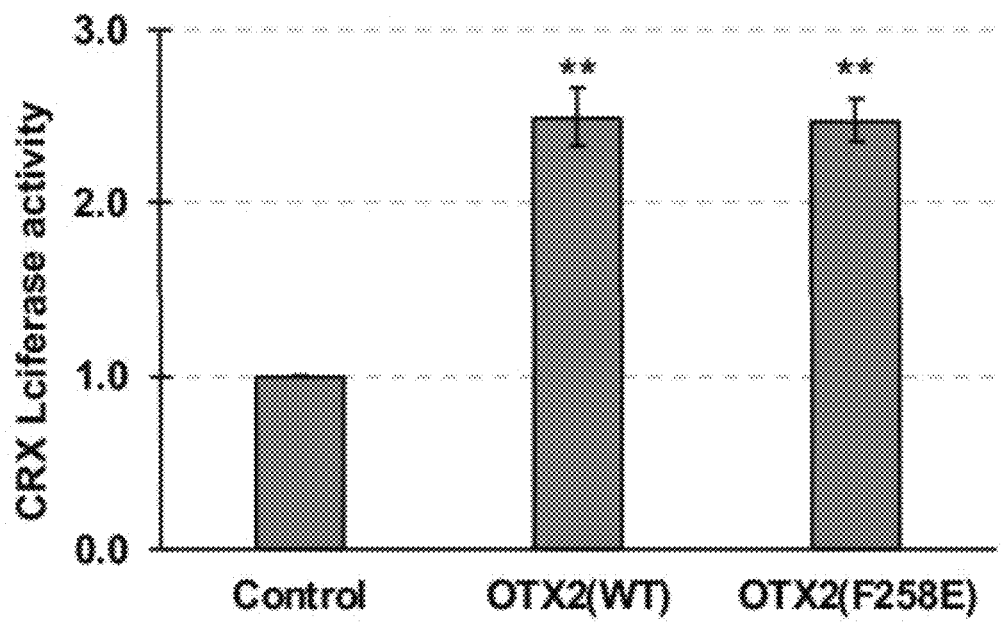
FIG. 10 illustrates the transcriptional activity of secretion-defective OTX2 (F258E) by measuring the activity of luciferase induced by the OTX2 target CRX promotor in transfected cells ($*p<0.01$; $p<0.005$; $*p<0.001$; ANOVA.)
Figure 11:
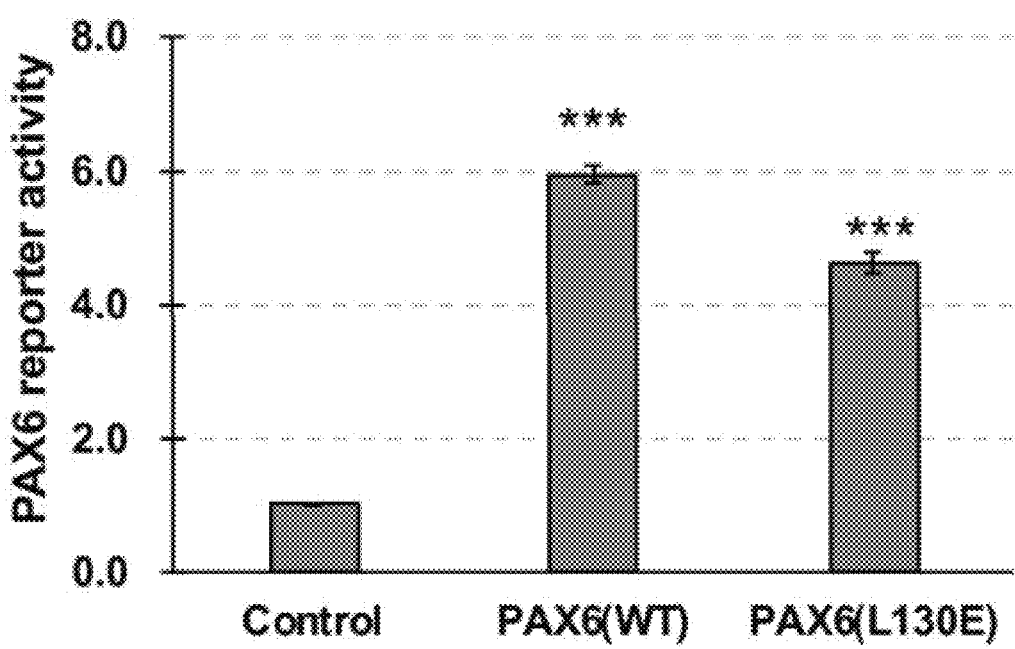
FIG. 11 illustrates the transcriptional activity of a PAX6 variant by measuring the activity of luciferase induced by a tandem PAX6 target DNA sequence ($*p<0.01$; $p<0.005$; $*p<0.001$; ANOVA.)

Further, as illustrated in FIGS. 10 and 11, OTX2 (F258E) and PAX6 (L130E) still showed transcriptional activities and induced luciferase reporter expression downstream of OTX2 target CRX promotor and tandem PAX6 binding sequences, respectively as strong as wild-type OTX2 and PAX6.

Figure 12:
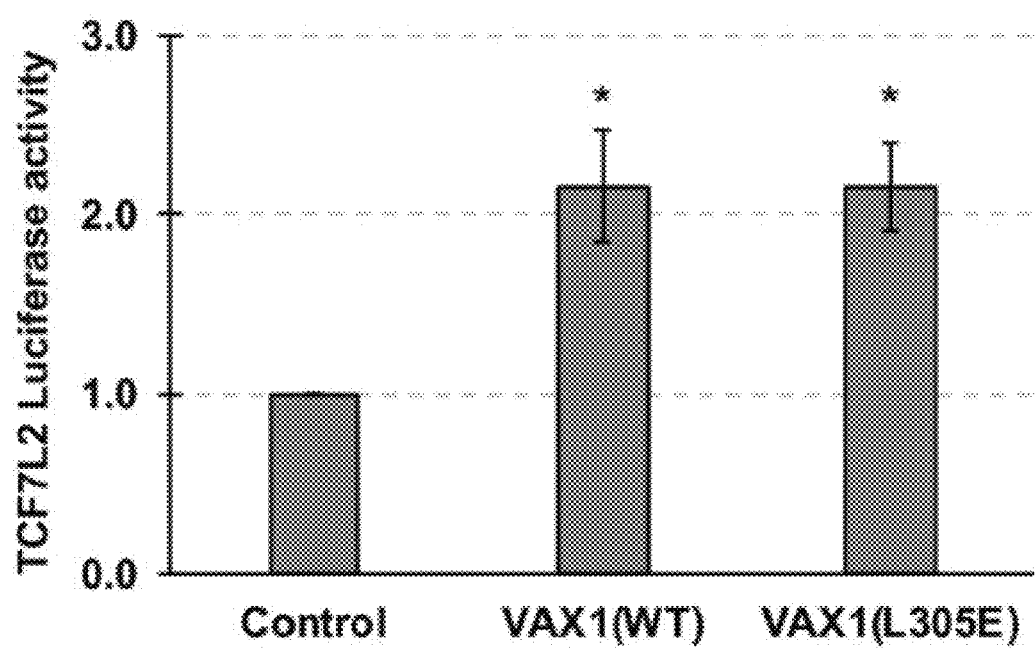
FIG. 12 illustrates the transcriptional activity of a VAX1 variant by measuring the activity of luciferase induced by a TCF7L2 promotor ($*p<0.01$; $p<0.005$; $*p<0.001$; ANOVA.)

In addition, as illustrated in FIG. 12, it was confirmed that VAX1 (L305E) also activated the expression of luciferase, whose transcription was regulated by a VAX1 target transcription factor 7-like 2 (TCF7L2) gene upstream sequence (Vacik et al., 2011), as significantly as wild-type VAX1.

The results suggest that the hydrophobic residues enhance extracellular secretion ability without affecting the transcriptional activities of the sHPs.

Next, the abilities of VAX1 (L305E) and wild-type VAX1 to affect retinal axon growth were compared, which is dependent on intercellular transfer of VAX1.

Figure 13:
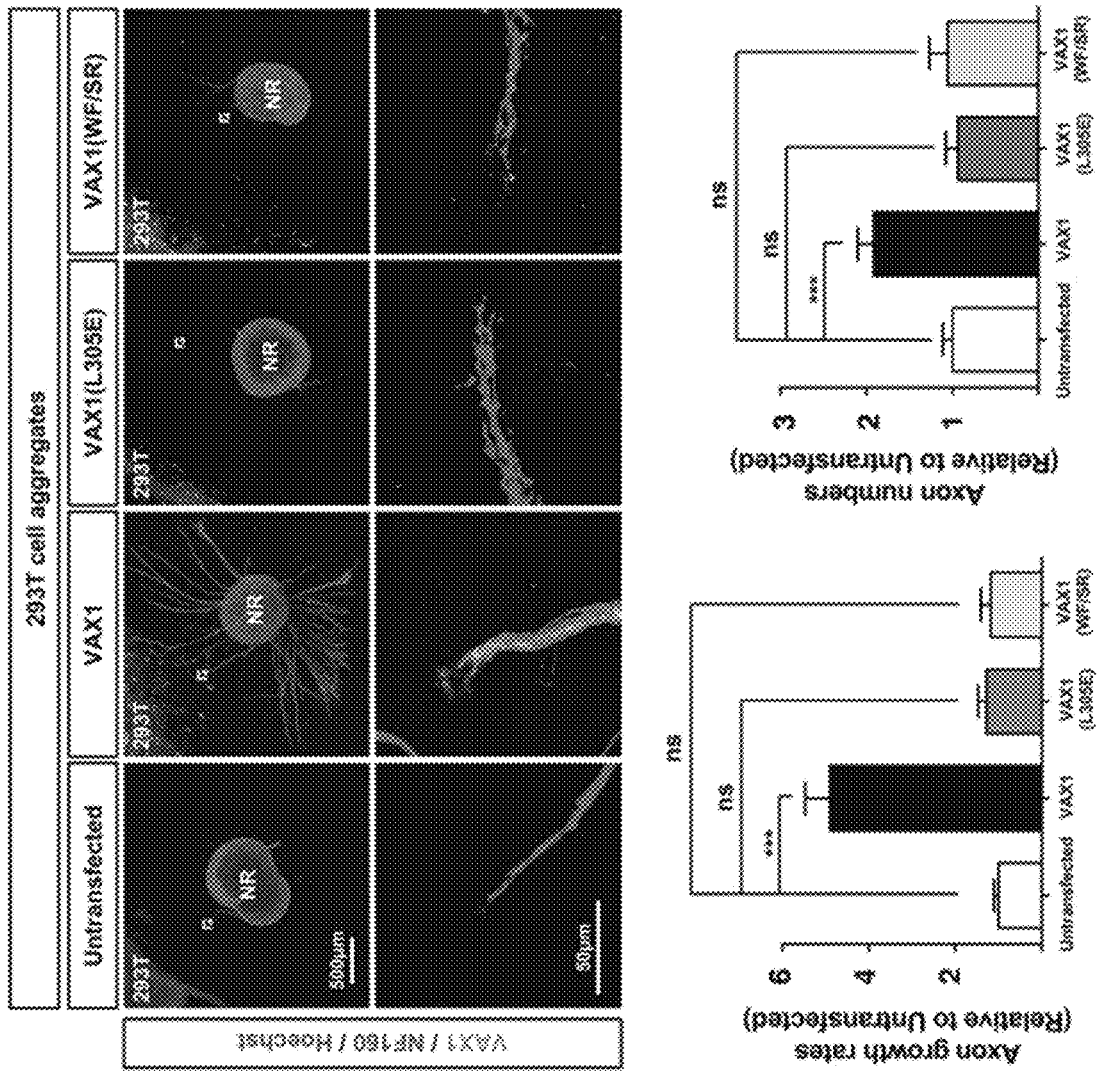
FIG. 13 illustrates the results of co-culturing 293T cells overexpressing V5-VAX1, V5-VAX1 (L305E) or V5-VAX1 (WFSR) with E13.5 mouse retinal explants for 48 hours ($*p<0.01$; $p<0.005$; $*p<0.001$; ANOVA.)
Figure 14:
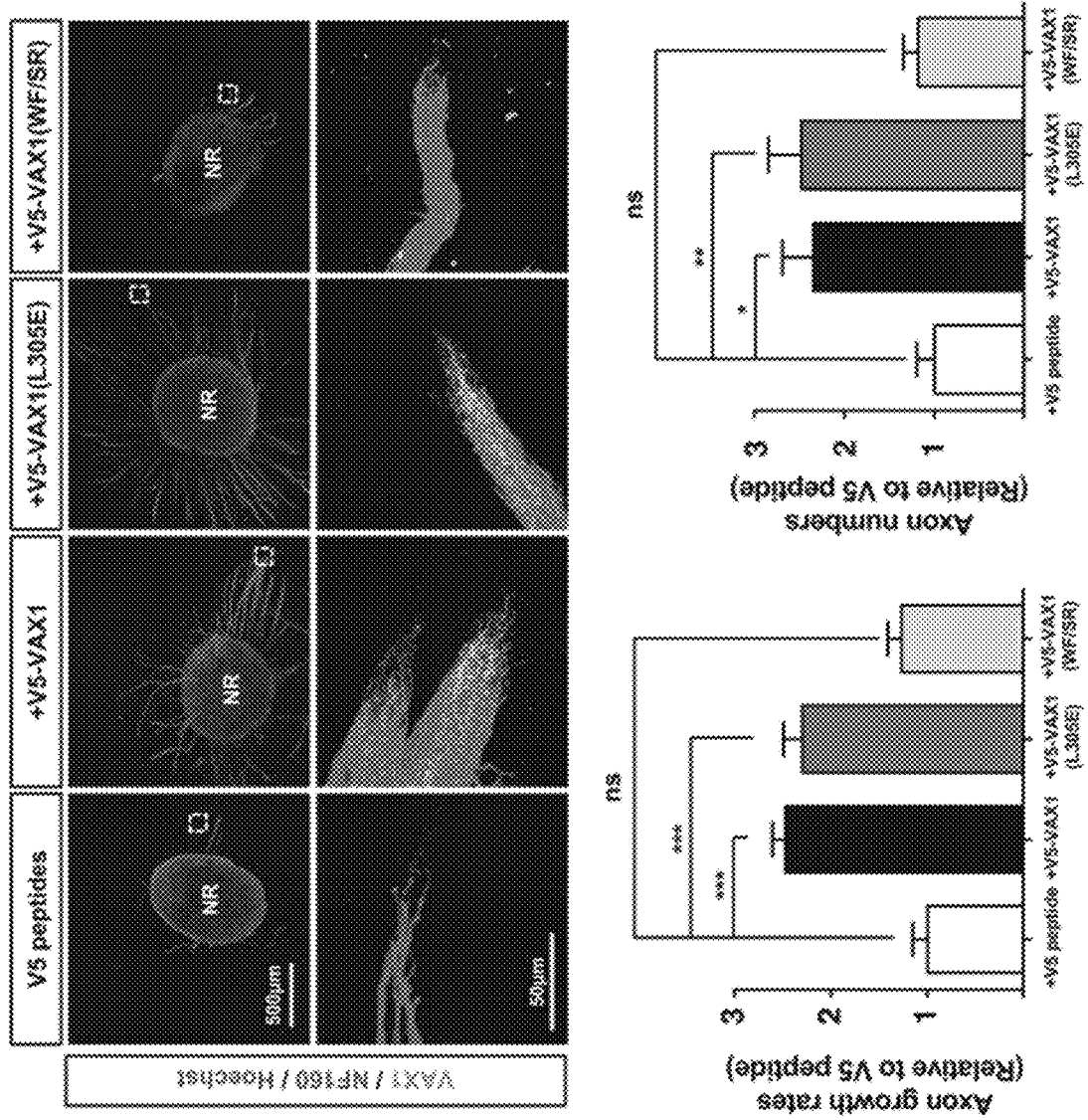
FIG. 14 illustrates the results of immunostaining of retinal explants treated with recombinant VS-tagged wild-type and mutant VAX1 proteins for 48 hours ($*p<0.01$; $p<0.005$; $*p<0.001$; ANOVA.).

V5-VAX1 overexpressed in 293T cells was detectable in the axons projecting from co-cultured mouse retinal explants as illustrated in FIG. 13, but V5-VAX1(L305E) proteins expressed in 293T cells were neither detectable in the retinal axons nor promoted the axonal growth. However, as illustrated in FIG. 14, recombinant V5-VAX1(L305E) added to the growth media of retinal explants was detectable in the retinal axons and induced axonal growth as efficiently as wild-type VAX1. On the contrary, it was confirmed that recombinant V5-VAX1(WF/SR), which can be secreted but cannot cross the cell membrane, was not detectable in the retinal axons, and it failed to induce axonal growth.

Collectively, the results suggest that VAX1(L305E) performs a normal transcription factor function in the nucleus, but cannot be secreted to the outside of the cells.

The present inventors have first elucidated that the presence or absence of a hydrophobic amino acid sequence outside the homeodomain as well as the homeodomain itself are associated with the factors which affect the extracellular secretion ability of homeoproteins, and confirmed that a homeoprotein whose extracellular secretion ability is increased or decreased could be induced through an increase or decrease in hydrophobicity of the amino acid sequence, and through research on the secretory mechanism of homeoproteins, the homeoprotein is expected to be usefully used to enhance the understanding of the secretory pathway by which various intracellular proteins which do not include secretory labels are secreted.

The above-described description of the present invention is provided for illustrative purposes, and those skilled in the art to which the present invention pertains will understand that the present invention can be easily modified into other specific forms without changing the technical spirit or essential features of the present invention. Therefore, it should be understood that the above-described embodiments are illustrative in all aspects and are not restrictive.

What is claimed is:

1. A homeoprotein variant whose extracellular secretion ability is increased or decreased, which is selected from the group consisting of the following variants:
   1) a variant in which amino acid 233 of a HOXD4 protein consisting of an amino acid sequence represented by SEQ ID NO: 1 has been substituted;
   2) a variant in which amino acid 305 of a SHOX2 protein consisting of an amino acid sequence represented by SEQ ID NO: 2 has been substituted;
   3) a variant in which amino acids 143 and 191 of a EN2 protein consisting of an amino acid sequence represented by SEQ ID NO: 3 have been substituted;
   4) a variant in which amino acid 220 or 258 of a OTX2 protein consisting of an amino acid sequence represented by SEQ ID NO: 4 has been substituted;
   5) a variant in which amino acid 130 of a PAX6 protein consisting of an amino acid sequence represented by SEQ ID NO: 5 has been substituted; and
   6) a variant in which amino acid 305 of a VAX1 protein consisting of an amino acid sequence represented by SEQ ID NO: 6 has been substituted.

2. The homeoprotein variant of claim 1, wherein the amino acid is substituted with a hydrophobic amino acid, thereby resulting in enhancement of extracellular secretion ability.

3. The homeoprotein variant of claim 1, wherein the amino acid is substituted with a hydrophilic amino acid, thereby resulting in a reduction of extracellular secretion ability.

4. The homeoprotein variant of claim 2, wherein the hydrophobic amino acid is leucine (Leu)(L).

5. The homeoprotein variant of claim 3, wherein the hydrophilic amino acid is glutamate (Glu)(E).

6. The homeoprotein variant of claim 1, wherein the homeoprotein variant is selected from the group consisting of:
   an amino acid sequence represented by SEQ ID NO: 7,
   an amino acid sequence represented by SEQ ID NO: 8,
   an amino acid sequence represented by SEQ ID NO: 9,
   an amino acid sequence represented by SEQ ID NO: 10,
   an amino acid sequence represented by SEQ ID NO: 11,
   an amino acid sequence represented by SEQ ID NO: 12, and
   an amino acid sequence represented by SEQ ID NO: 13.

7. A method for increasing or decreasing extracellular secretion ability of a homeoprotein, the method comprising any one step selected from the group consisting of the following steps:
   1) substituting amino acid 223 of a HOXD4 protein consisting of an amino acid sequence represented by SEQ ID NO: 1;
   2) substituting amino acid 305 of a SHOX2 protein consisting of an amino acid sequence represented by SEQ ID NO: 2;
   3) substituting amino acids 143 and 191 of a EN2 protein consisting of an amino acid sequence represented by SEQ ID NO: 3;
   4) substituting amino acid 220 or 258 of a OTX2 protein consisting of an amino acid sequence represented by SEQ ID NO: 4;
   5) substituting amino acid 130 of a PAX6 protein consisting of an amino acid sequence represented by SEQ ID NO: 5; and
   6) substituting amino acid 305 of a VAX protein consisting of an amino acid sequence represented by SEQ ID NO: 6.

8. A method for predicting extracellular secretion ability of a homeoprotein, the method comprising any one step selected from the group consisting of the following steps:
   1) confirming whether amino acid 223 of a HOXD4 protein consisting of an amino acid sequence represented by SEQ ID NO: 1 is a hydrophobic amino acid;
   2) confirming whether amino acid 305 of a SHOX2 protein consisting of an amino acid sequence represented by SEQ ID NO: 2 is a hydrophobic amino acid;
   3) confirming whether amino acids 143 and 191 of a EN2 protein consisting of an amino acid sequence represented by SEQ ID NO: 3 are hydrophobic amino acids;
   4) confirming whether amino acid 220 or 258 of a OTX2 protein consisting of an amino acid sequence represented by SEQ ID NO: 4 is a hydrophobic amino acid;
   5) confirming whether amino acid 130 of a PAX6 protein consisting of an amino acid sequence represented by SEQ ID NO: 5 is a hydrophobic amino acid; and
   6) confirming whether amino acid 305 of a VAX1 protein consisting of an amino acid sequence represented by SEQ ID NO: 6 is a hydrophobic amino acid.
   an amino acid sequence represented by SEQ ID NO: 13.

* * * * *